(12) United States Patent
Brunner et al.

(10) Patent No.: US 7,415,361 B2
(45) Date of Patent: Aug. 19, 2008

(54) METHODS AND SYSTEMS FOR ANALYZING AND DETERMINING LIGAND-RESIDUE INTERACTION

(75) Inventors: Stephan Brunner, Préverenges (CH); David Mosenkis, Philadelphia, PA (US); Frank P. Hollinger, Wayne, PA (US); William Chiang, Pennington, NJ (US)

(73) Assignee: Locus Pharmaceuticals, Inc., Blue Bell, PA (US)

(*) Notice: Subject to any disclaimer, the term of this patent is extended or adjusted under 35 U.S.C. 154(b) by 9 days.

(21) Appl. No.: 10/920,234

(22) Filed: Aug. 18, 2004

(65) Prior Publication Data

US 2005/0123995 A1 Jun. 9, 2005

Related U.S. Application Data

(63) Continuation-in-part of application No. 10/730,267, filed on Dec. 9, 2003, now abandoned.

(51) Int. Cl.
*G06F 17/00* (2006.01)
*G06F 17/30* (2006.01)
(52) U.S. Cl. .......................... 702/27; 702/19
(58) Field of Classification Search ............. 702/19, 702/27
See application file for complete search history.

(56) References Cited

U.S. PATENT DOCUMENTS

| | | | |
|---|---|---|---|
| 5,557,535 | A | 9/1996 | Srinivasan et al. |
| 5,600,571 | A | 2/1997 | Friesner et al. |
| 5,854,992 | A | 12/1998 | Shakhnovich et al. |
| 5,884,230 | A | 3/1999 | Srinivasan et al. |
| 6,029,114 | A | 2/2000 | Shamovsky et al. |
| 6,178,384 | B1 | 1/2001 | Kolossváry |
| 6,251,620 | B1 | 6/2001 | Hatada et al. |
| 6,341,256 | B1 | 1/2002 | Deem et al. |
| 6,426,205 | B1 | 7/2002 | Tyers et al. |
| 6,489,608 | B1 | 12/2002 | Silling |
| 6,640,191 | B1 | 10/2003 | Deem et al. |
| 6,716,614 | B1 | 4/2004 | Donoho et al. |
| 6,735,530 | B1* | 5/2004 | Guarnieri ................ 702/27 |
| 2002/0099506 | A1* | 7/2002 | Floriano et al. ............. 702/19 |
| 2003/0055574 | A1 | 3/2003 | Still et al. |
| 2004/0267456 | A1 | 12/2004 | Brunner et al. |

FOREIGN PATENT DOCUMENTS

| | | |
|---|---|---|
| EP | 0 807 687 A2 | 11/1997 |
| WO | WO 96/34347 A1 | 10/1996 |
| WO | WO 97/16177 A1 | 5/1997 |
| WO | WO 2004/078932 A1 | 9/2004 |
| WO | WO 2004/081841 A1 | 9/2004 |

OTHER PUBLICATIONS

Abagyan et al. Curr Opin Chem Biol. Aug. 2001;5(4):375-82.*
Apostolakis et al Journal of Computational Chemistry, vol. 19, No. 1, 21-37,1998.*
Fahmy et al Journal of the American Chemical Society (2002), 124(7), 1241-1250.*
Knegtel et al. Journal of Computer-Aided Molecular Design, 13: 167-183, 1999.*
Adachi, M., et al., "A novel methodology for assisting in the discovery of new chromogens: theoretical calculations with high throughput screening," *Advances in Colour Science and Technology* 4:124-129, University of Leeds (2001).
Adams, D.J., "Grand canonical ensemble Monte Carlo for a Lennard-Jones fluid," *Mol. Phys.* 29:307-311, Taylor & Francis Ltd. (1975).
Apostolakis, J., et al., "Computational Ligand Design," *Combinatorial Chemistry and High Throughput Screening* 2:91-104, Bentham Science Publishers B.V. (1999).
Basson, I. and Reynhardt, E.C., "NMR of montan wax," *J. Phys. D: Appl. Phys.* 21:1434-1437, IOP Publising Ltd. (1998).
Basson, I. and Reynhardt, E.C., "An investigation of the structures and molecular dynamics of natural waxes: III. Montan wax," *J. Phys. D: Appl. Phys.* 21:1434-1437, IOP Publishing Ltd. (1988).
Blaskó, A., et al., "Pendant-Capped Porphyrins.2.Structural Analysis and Dynamics of the Biphenyl Pendant-Capped Porphyrin Model of Catalase and Its Fe (III) Complex by One- and Two-Dimensional 1H NMR Spectroscopy and Distance Geometry/Molecular Modeling Refinement," *J. Am. Chem.* 58:5738-5747, American Chemical Society (1993).
Brandmeier, V., et al., "8. Antiparallel β-Sheet Conformation in Cyclopeptides Containing a Pseudo-amino Acid with Biphenyl Moiety," *Helv. Chim. Acta* 77:70-85, Neu Schweizerische Chemische Gesellschaft (1994).
Bredikhin, A., et al., "Molecular and Crystalline Structure of Dimethyl 4,6-Dimethyl-2-(2-nitrophenyl)-1,2-dihydropyridine-3,5-dicarboxylate, By-product in the Synthesis of Nifedipine," *Russian Journal of Organic Chemistry* 35:1372-1376, Ma ⁄k "Hayka/Interperiodica" (1999).
Caflisch, A., et al., "Multiple Copy Simultaneous Search and Construction of Ligands in Binding Sites: Application to Inhibitors of HIV-1 Aspartic Proteinase," *J. Med. Chem.* 36:2142-2167, American Chemical Society (1993).
Calafat, A.M., et al., "A New Arrangement for the Anticancer Antibiotics Tallysomyein and Bleomycin When Bound to Zinc: An Assessment of Metal and Ligand Chirality by NMR and Molecular Dynamics," *J. Am. Chem. Soc.* 119:3656-3664, American Chemical Society (1997).

(Continued)

*Primary Examiner*—Michael Borin
(74) *Attorney, Agent, or Firm*—Pepper Hamilton LLP

(57) ABSTRACT

A method implemented in the form of a computer simulation code for evaluating the free energy of binding between polypeptide amino acid residues and one or more molecular fragment types is presented. The basis of the method is a novel weighted Metropolis Monte Carlo approach for sampling the grand canonical ensemble. By making use of the properties of the grand canonical ensemble, the affinity of fragments for binding in the vicinity of each protein residue can be efficiently computed. The binding volume associated to each fragment-residue pair is estimated on the basis of a simple proximity criteria, and a useful affinity mapping of the protein surface can be obtained in this way. The analysis of such data for various fragment types provides valuable information to help identify protein binding sites, as well as to identify key fragments used for building potential drug leads.

13 Claims, No Drawings

OTHER PUBLICATIONS

Catlow, C., et al., "Computer Modeling of Nucleation, Growth, and Templating in Hydrothermal Synthesis," *Chem. Mater.* 10:3249-3265, American Chemical Society (1998).

Clough, S.B., et al., "Molecular Dynamics Simulation of Substituted Conjugated Ionic Polyacetylenes," *Macromolecules* 26:597-600, American Chemical Society (1993).

Chan, D.C., et al., "Core Structure of gp41 from the HIV Envelope Glycoprotein," *Cell* 89:263-273, Cell Press (1997).

Chen, B., et al., "Synthesis of Specifically Deuterated Nucleotides and Their Application in Mechanistic Elucidation of DNA and RNA Cleavage by the Hydroxyl Radical," Abstract No. 116, Book of Abstracts, American Chemical Society, *224th ACS National Meeting*, Boston, MA (Aug. 18-22, 2002).

Dennis, S., et al., "Computational mapping identifies the binding sites of organic solvents on proteins," *Proc. Natl. Acad. Sci. USA* 99:4290-4295, National Academy of Sciences (Apr. 2002).

Ding, X., et al., "Nature of the Inactivation of Elastase by $N$-Peptidyl O aroyl hydroxylamine as a Function of pH," *Biochem.* 34:7749-7756, American Chemical Society (1995).

Duggan, H. and Craik, D.J., "$^1$H and $^{13}$C NMR Relaxation Studies of Molecular Dynamics of the Thyroid Hormones Thyroxine, 3, 5, 3'-Triiodothyronine, and 3,5,-Diiodothyronine," *J. Med. Chem.* 39:4007-4016, American Chemical Society (1996).

Edwards and Burnstein, "Synthetic Inhibitors of Elastase," *Med. Res. Rev.* 14:127-194, John Wiley & Sons, Inc. (1994).

Gibson, K.D. and Scheraga, H.A., "Crystal Packing without Symmetry Constraints.2. Possile Crystal Packings of Benzene Obtained by Energy Minimization from Multiple Starts," *J. Phys. Chem.* 99:3765-3773, American Chemical Society (1995).

Guarnieri, F., and Mezei, M., "Simulated Annealing of Chemical Potential: A General Procedure for Locating Bound Waters. Application to the Study of the Differential Hydration Propensities of the Major and Minor Grooves of DNA," *J. Am. Chem. Soc.* 118:8493-8494, American Chemical Society (1996).

Henson, N., et al., "Computational Studies of Cobalt-Substituted Aluminophosphates," *J. Phys. Chem. A* 104:2423-2431, American Chemical Society (2000).

Honma, T., "Recent Advances in De Novo Design Strategy for Practical Lead Identification," *Med. Res. Rev.* 23:606-632, Wiley Periodicals, Inc. (Sep. 2003).

Huang, C.C., et al., "Integrated Tools for Structural and Sequence Alignment and Analysis," *Pacific Symposium on Biocomputing*, presented at the *Pacific Symposium on Biocomputing*, Oahu, Hawaii, pp. 230-241 (2000).

Johnson, P.M., "Resonance ionization spectra as a reflection of excited state dynamics," *Inst. Phys. Conf.* Ser. No. 114: Section 4:145-150, presented at the *Proceedings of the Fifth International Symposium on Resonance Ionization Spectroscopy and its Applications*, Congress Centre Villa Ponti, Varese, Italy (1990).

Joseph-McCarthy, D., et al., "Use of MCSS to Design Small Targeted Libraries: Application to Picornavirus Ligands," *J. Am. Chem. Soc.* 123:12758-12769, American Chemical Society (2001).

Koone, N., et al., "Diffusion of Simple Liquids in Porous Sol-Gel Glass," *J. Phys. Chem.* 99:16976-16981, American Chemical Society (1995).

Kortemme, T., and Baker, D., "A simple physical model for binding energy hot spots in protein-protein complexes," *Proc. Natl. Acad. Sci. USA* 99:14116-14121, National Academy of Sciences (Oct. 2002).

Kortemme, T., and Baker, D., "A simple physical model for binding energy hot spots in protein-protein complexes," *Proc. Natl. Acad. Sci. USA* 99:14116-14121, National Academy of Sciences (Oct. 2002).

Lee, T. and Jones, J.B., "Probing the Abilities of Synthetically Useful Serine Proteases to Discriminate between the Configurations of Remote Stereocenters Using Chiral Aldehyde Inhibitors," *J. Am. Chem. Soc.* 118:502-508, American Chemical Society (1996).

Lee, Y.-C., et al., "Computational Studies of Polyelectrolytes Containing Zeolitic Fragments," *J. Phys. Chem. B* 103:6445-6449, American Chemical Society (1999).

Lynch, G.C. and Pettit, B.M., "Grand canonical ensemble molecular dynamics simulations: Reformulation of extended system dynamics approaches," *J. Chem. Phys.* 107:8594-8610, American Chemical Society (1997).

Lunazzi, L., et al., "Conformational Studies by Dynamic NMR, 58.[1] Steeodynamics of C-C and C-N Rotation in Furan and Thiophene $o$-Amino Thioaldehydes and Aldehydes," *J. Org. Chem.* 62:2263-2266, American Chemical Society (1997).

Massova, I., and Kollman, P.A., "Computational Alanine Scanning to Probe Protein Protein Interactions: A Novel Approach To Evaluate Binding Free Energies," *J. Am. Chem. Soc.* 121:8133-8143, American Chemical Society (1999).

Mattos, C., et al., "Analogous inhibitors of elastase do not always bind analogously," *Struct. Biol.* 1:55-58, Nature Publishing Company (1994).

Mattos, C., et al., "Structural Analysis of the Active Site of Porcine Pancreatic Elastase Based on the X-ray Crystal Structures of Complexes with Trifluoroacetyl- Dipeptide-Anilide Inhibitors," *Biochemistry* 34:3193-3203, American Chemical Society (1995).

Mehrotra, P.K. and Beveridge, D.L., "Structural Analysis of Molecular Solutions Based on Quasi-Component Distribution Functions. Application to $[H_2O]_{aq}$ at 25° C.," *J. Am. Chem. Soc.* 102:4287-4294, American Chemical Society (1980).

Metropolis, N., et al., "Equation of State Calculations by Fast Computing Machines," *J. Chem. Phys.* 21:1087-1092, American Institute of Physics (1953).

Mezei, M., "Grand-canonical ensemble Monte Carlo study of dense liquid Lennard-Jones, soft spheres and water," *Mol. Phys.* 61:565-582, Taylor & Francis Ltd. (1987).

Mezei, M. and Beveridge, D.L., "Structural Chemistry of Bimolecular Hydration via Computer Simulation: The Proximity Criterion," in *Methods in Enzymology*, Packer, ed., Academic Press, NY, pp. 21-47, (1986).

Mezei, M., "Modified Proximity Criteria for the Analysis of the Solvation of a Polyfunctional Solute," *Mol. Simul.* 1:327-332, Gordon and Breach Science Publishers S.A. (1988).

Mezey, P., "Relations between Computational and Experimental Engineering Approaches to Molecules from Molecular Fragments," *Molecular Engineering* 8:235-250, Kluwer Academic Publishers (1999).

Miranker, A., and Karplus, M., "Functionality Maps of Binding Sites: A Multiple Copy Simultaneous Search Method," *Proteins* 11:29-34, Wiley-Liss, Inc. (1991).

Mokrosz, J.L., et al., "Conformational Analysis of 4-(2'-Furyl)-2-(methylamino) pyrimidine," *J. Heterocyclic Chem.* 33:1207-1210, HeteroCorporation (1996).

Morgantini, P.-Y. and Kollman, P.A., "Solvation Free Energies of Amides and Amines: Disagreement between Free Energy Calculations and Experiment," *J. Am. Chem. Soc.* 117:6057-6063, American Chemical Society (1995).

Petoukhov et al., "Addition of Missing Loops and Domains to Protein Models by X-Ray Solution Scattering," *Biophys. J.* 83:3113-3125, Biophysical Society (Dec. 2002).

Raineri, F.O., et al., "Surrogate Hamilitonian description of solvation dynamics. Resolution of global responses into spatial profiles," *Chem. Phys.* 183:187-205, Elsevier Science B.V. (1994).

Resat, H. and Mezei, M., "Grand Canonical Ensemble Monte Carlo Simulation of the dCpG/Proflavine Crystal Hydrate," *Biophys. J.* 71:1179-1190, Biophysical Society (1996).

Resat, H. and Mezei, M., "Grand canonical Monte Carlo Simulation of Water Positions in Crystal Hydrates," *J. Am. Chem. Soc.* 116:7451-7452, American chemical Society (1994).

Resat, H., et al., "Use of the Grand Canonical Ensemble in Potential of Mean Force Calculations," *J. Phys. Chem.* 100:1426-1433, American Chemical Society (1996).

Siepmann, J.I. and McDonald, I.R., "Monte Carlo study of the properties of self-assembled monolayers formed by adsorption of $CH_3(CH_2)_{15}SH$ on the (111) surface of gold," *Mol. Phys.* 79:457-473, Taylor and Francis Ltd. (1993).

Vaidehi, N., et al., "Prediction of structure and function of G protein-coupled receptors," *Proc. Natl. Acad. Sci.* 99:12622-12627, National Academy of Sciences (Oct. 2002).

Verkhivker, G.M., et al., "Monte Carlo Simulations of the Recognition at the Consensus Binding Site of the Constant Fragment of Human Immunoglobulin G: the Energy Landscape Analysis of a Hot Spot at the Intermolecular Interface," *Proteins: Structure, Function, and Genetics* 48:539-557, Wiley-Liss, Inc. (Aug. 2002).

International Preliminary Examination Report for International Application No. PCT/US2003/07366, IPEA, Alexandria, VA, mailed on May 25, 2005.

International Search Report for International Application No. PCT/US2003/07366, International Search Authority, Alexandria, VA, mailed on Oct. 30, 2003.

International Search Report for International Application No. PCT/US2004/06347, International Search Authority, Alexandria, VA, mailed on Apr. 12, 2005.

International Search Report for International Application No. PCT/US2004/14069, International Search Authority, Alexandria, VA, mailed on Oct. 8, 2004.

Office Action for U.S. Appl. No. 09/183,267, inventor Guarnieri, F., filed Oct. 30, 1998, mailed on Jun. 30, 2000.

Office Action for U.S. Appl. No. 09/183,267, inventor Guarnieri, F., filed Oct. 30, 1998, mailed on Mar. 5, 2001.

Office Action for U.S. Appl. No. 09/183,267, inventor Guarnieri, F., filed Oct. 30, 1998, mailed on Mar. 12, 2003.

Office Action for U.S. Appl. No. 09/722,731, inventor Guarnieri, F., filed Nov. 28, 2000, mailed on Sep. 26, 2002.

Office Action for U.S. Appl. No. 09/722,731, inventor Guarnieri, F., filed Nov. 28, 2000, mailed on Aug. 30, 2005.

Goodsell, D.S. and Olson, A.J., "Automated Docking of Substrates to Proteins by Simulated Annealing," *Proteins: Structure, Function, and Genetics* 8:195-202, Wiley-Liss, Inc. (1990).

Meng, E.C., et al., "Automated Docking with Grid-Based Energy Evaluation," *J. Comp. Chem.* 13:505-524, John Wiley & Sons, Inc. (1992).

Nilges, M., et al., "Determination of three-dimensional structures of proteins from interproton distance data by dynamical simulated annealing from a random array of atoms," *FEBS Lett.* 239:129-136, Elsevier Science Publishers B.V. (1988).

Co-pending U.S. Appl. No. 09/722,731, inventor Guarnieri, F., filed Nov. 28, 2000 (Not Published).

Co-pending U.S. Appl. No. 10/791,681, inventor Hollinger, F., filed Mar. 3, 2004 (Not Published).

Co-pending U.S. Appl. No. 10/813,553, inventors Ludington, J., et al., filed Mar. 31, 2004 (Not Published).

Co-pending U.S. Appl. No. 11/146,417, inventors Guarnieri, F., et al., filed Jun. 7, 2005 (Not Published).

* cited by examiner

METHODS AND SYSTEMS FOR ANALYZING AND DETERMINING LIGAND-RESIDUE INTERACTION

CROSS REFERENCE TO RELATED APPLICATIONS

This application is a continuation-in-part of U.S. application Ser. No. 10/730,267 filed Dec. 9, 2003, now abandoned which is hereby incorporated by reference in its entirety.

BACKGROUND OF THE INVENTION

1. Field of the Invention

The present invention relates to computer-implemented methods and systems for analyzing the interaction between polypeptide amino acid residues and one or more molecular fragments. The invention further provides methods and systems for using the information regarding the fragment-polypeptide interaction to aid in drug design.

2. Related Art

The action of a particular drug is believed to result from the interaction of that drug with a particular molecular target, such as a protein, nucleic acid, or other molecule found in the biological system. Typical protein drug targets include enzymes and receptors (Thomas G., "Medicinal Chemistry—An Introduction" (John Wiley & Sons, Ltd., New York, 2001)).

In the case of an enzyme, its binding with a drug molecule usually has the effect of interfering with the normal operation of that enzyme. The drug molecule may bind directly within the active site of the enzyme or act indirectly by binding to a so-called allosteric site. Similarly, drugs may act on a receptor by binding to, or near, its surface. This may either activate the receptor, or prevent the binding of its normal substrate to that receptor. Ultimately, such drug actions can result in a physiological response with the purpose of providing a therapeutic effect.

The drug's effectiveness will depend on the stability of the drug-enzyme or drug-receptor complex, as well as the number of binding sites occupied by the drug. Other targets for drug action include nucleic acids and other naturally occurring molecules.

To rationally develop a drug lead, it is therefore desirable to have accurate knowledge of the binding site(s) on the target molecule (e.g., enzyme, receptor or nucleic acid). One method used for determining protein binding sites is so-called protein mapping, where different molecular probes, typically small organic molecules representing various functional groups, are placed around the protein surface to determine the most favorable binding positions (Dennis et al., *PNAS* 99:4290-4295 (2002)). Experimental approaches to protein mapping include x-ray crystallography and NMR methods. Both of these approaches have shown that probes, even those generally unrelated to any natural substrate of the protein, bind only to a limited number of positions. Generally, a pocket of the active site tends to form a consensus site that binds many ligands, regardless of their sizes and polarities.

Because of major difficulties associated in many cases with co-crystallizing proteins and probes, or using NMR for determining binding sites, a number of methods have been developed to perform mapping computationally rather than experimentally. Examples of such computer codes are the drug design program GRID (Goodford, P. J., *J. Med. Chem.* 28:849-875 (1985)), or the Multiple Copy Simultaneous Search (MCSS) strategy (Miranker, A. & Karplus, M., *Proteins Struct. Funct. Genet.* 11:29-34 (1991); Caflish, A., et al., *J. Med. Chem.* 36:2142-2167 (1993); Joseph-McCarthy, D., et al., *J. Am. Chem. Soc.* 123:12758-12769 (2001)).

The main problem with the computational approaches referenced above is that they are usually limited to identifying the many local minima along the protein surface of the potential energy field representing the fragment-protein interaction. This data lacks the essential information required for determining which of these minima represents a biologically relevant binding site. (Dennis et al., *PNAS* 99:4290-4295 (2002)). Indeed, although computationally more expeditious, energy minimization approaches are unable to correctly estimate free energies of binding, which, as presented further on, is the basic biologically relevant quantity for characterizing the binding affinity of a ligand. To estimate a free energy of binding, information on the actual thermodynamic fragment distributions around the protein, i.e., distributions consistent with thermal fluctuations at physiological temperatures, is required. Such thermodynamic distributions provide information on entropic effects, necessary for free energy calculations.

Accordingly, improved computational methods are necessary to provide accurate and efficient estimates of the free energy of binding of molecular fragments to protein binding sites, so that high affinity ligands can be designed for these sites.

SUMMARY OF THE INVENTION

Recognizing the essential need for relevant characterization of the interaction between fragments and polypeptide molecules, the computational method of the present invention estimates the affinity of particular fragment-residue pairs, which enables the identification of key fragment interactions with the protein based on an analysis of computed fragment-residue interactions. When analyzed appropriately as described below, potential binding sites can be identified and the identification of the important fragments, which can be viewed as key pharmacophore elements, are assembled into potential drug leads. These same affinity values also provide a useful numerical convergence criteria, i.e., an assessment of the statistical validity of a given simulation, as well as a quantitative diagnostic to compare the results from different simulations.

The present invention includes conducting a computer simulation of the interaction between (i) a polypeptide and (ii) at least one type of molecular fragment, wherein a sampling from a thermodynamic ensemble of states of the polypeptide-fragment system is collected; and an affinity value is then computed and assigned to at least one fragment-residue pair when the fragment has a finite probability of being in the vicinity of the residue, wherein the affinity value is a measure of the free energy of interaction between the polypeptide and the fragment; wherein the above calculations are conducted for each type of molecular fragment considered.

Alternatively, the invention provides methods and systems for analyzing one or more samplings from a thermodynamically relevant ensemble for a ligand, or fragment, interacting with a residue of a polypeptide or a protein.

The present invention further provides methods and systems for using the affinity values of the present invention to identify protein binding sites, and help determine the key fragments to be used in constructing ligands for a given polypeptide molecule. Finally, the affinity values can also be used as a numerical convergence criterion for a given simulation, as a diagnostic to compare the results from multiple computer-implemented simulations, and to identify protein binding sites and help determine the key fragments to use in constructing ligands for a given polypeptide.

DETAILED DESCRIPTION OF THE INVENTION

I. Overview

Terms are used herein as generally used in the art, unless otherwise defined herein.

In one aspect, the present invention provides methods and systems for analyzing the affinity between polypeptide amino acid residues and one or more molecular fragment types. In one embodiment, the present invention includes conducting a computer simulation of the interaction between (i) a polypeptide, and (ii) at least one type of molecular fragment, wherein a sampling from a thermodynamic ensemble of states of the polypeptide-fragment system is collected; and an affinity value is then computed and assigned to at least one fragment-residue pair when the fragment has a finite probability of being in the vicinity of the residue, wherein the affinity value is a measure of the free energy of interaction between the polypeptide and the fragment; wherein the above calculations are conducted for each type of molecular fragment considered.

Alternatively, the invention provides methods and systems for analyzing one or more samplings from a thermodynamically relevant ensemble for a ligand, or fragment, interacting with a residue of a polypeptide or a protein.

As used herein, the term "polypeptide" encompasses a molecule comprised of amino acid molecules linked by peptide bonds, and includes all such molecules, regardless of the number of amino acids in the molecule. The term polypeptide, as used herein, also includes molecules which include other moieties in addition to amino acids, an example being glycosylated polypeptides such as antibodies. The term polypeptide, as used herein, also includes protein molecules which consist of more than one chain of amino acids linked by peptide bonds; the multiple chains may be covalently bonded to each other by means of disulfide side-chain bonds.

"Fragments," as the term is used herein, includes molecules or molecular fragments (e.g. radicals) that can be used to model one or more types of interaction with a macromolecule, such as the interactions of carbonyls, hydroxyls, amides, hydrocarbons, and the like. Examples of useful fragments include, but are not limited to:

| Name | Structure |
|---|---|
| Acetone | $CH_3(C=O)CH_3$ |
| Aldehyde | $H(C=O)-CH_3$ |
| Amide | $H(C=O)NH_2$ |
| Ammonia | $NH_3$ |
| Benzene | 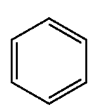 |
| Carboxylic Acid | $CH_3COOH$ |
| 1,4-Diazine | 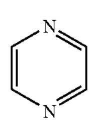 |
| Ester | $CH_3-O-(C=O)-CH_3$ |
| Ether | $CH_3-O-CH_3$ |
| Formaldehyde | $H_2C=O$ |

-continued

| Name | Structure |
|---|---|
| Furan | 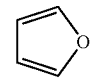 |
| Imidazole | 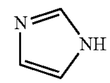 |
| Methane | $CH_4$ |
| Methanol | $CH_3OH$ |
| Phospho-Acid | 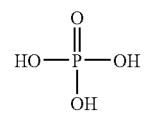 |
| Pyridine | 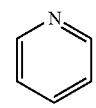 |
| Pyrimidine | 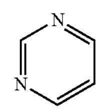 |
| Thiol | $CH_3SH$ |
| Thiophene | 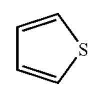 |

The fragments are preferably selected to represent chemical features that have proven useful in the design of pharmaceuticals or other bioactive chemicals. Additional possible fragment types of interest will be readily apparent to one skilled in the art.

A database of organic fragments relevant for drug discovery has been compiled by extracting organic fragments from molecules published in 1) the *Journal of Medicinal Chemistry* from 1991-2001, 2) *Journal of Heterocyclic Chemistry* from 1981-2001, 3) *Medicinal Research Reviews* from 1991-2001 and 4) heterocyclic chemistry text books (for example, Eicher, T.; Hauptmann, S. *The Chemistry of Heterocycles; Thieme Organic Chemistry Monograph Series:* 1995) and other journals and texts covering biologically active molecules. The compiled database is regularly augmented with new fragments from the literature, as well as new fragments tailored in an iterative process for a specific target macromolecule thanks to information obtained from previous simulations of the type described herein, as well as new fragments resulting from modifications that a chemist would consider for issues such as synthetic tractability.

In one aspect of the methods of the present invention, a computer simulation of the interaction between a polypeptide and at least one type of molecular fragment is conducted, wherein at least one sampling of states from a thermodynamic ensemble representing the polypeptide-fragment system is collected. In one aspect of the present invention the ensemble sampling of the protein-fragment system is obtained through a Metropolis Monte Carlo-type method. (Metropolis, N., et al., *J. Chem. Physics* 21:1087-1092 (1953), U.S. Pat. No. 6,735,530). Such a computation is repeated for a large collection of different organic fragment types with diverse physico-chemical properties. The number of fragment types can be in the hundreds to thousands.

For each sampled state of the rigid fragment a set of attributes is saved, including the relative position and orientation with respect to the protein, as well as the potential energy of interaction between the fragment and the protein. The fragment's position can be characterized by the coordinates (x,y,z) of its center of mass, while its orientation is conveniently represented by a unit quaternion q.

This Monte Carlo data for the different fragment types is analyzed for identifying potential binding sites using the methods of the present invention. These tools are based on the postulate that a binding site must be a localized high affinity region for a diverse collection of fragment types, i.e., fragments with different physico-chemical properties. In one aspect the binding site may also be determined by the ability of a diverse collection of fragment types to be coincident in a region of the protein where bound water molecules can freely exchange with bulk water. In one aspect, additional experimental binding site data, such as co-crystal X-ray data and/or residue mutational analysis, if available, is used to help in determining the final site within which the leads are designed.

The actual relevant thermodynamic fragment distributions around the protein, i.e., distributions consistent with thermal fluctuations at physiological temperatures, can be computed numerically using a Metropolis Monte Carlo approach (Metropolis, N., et al., J. Chem. Physics 21:1087-1092 (1953)). Information on the thermodynamic distribution is essential for computing free energies of binding, which is the basic biologically relevant quantity for quantifying the binding affinity of a ligand. By contrast, the MCSS approach (Miranker, A. & Karplus, M., Proteins Struct. Funct. Genet. 11:29-34 (1991); Caflish, A., et al., J. Med. Chem. 36:2142-2167 (1993); Joseph-McCarthy, D., et al., J. Am. Chem. Soc. 123:12758-12769 (2001)), for example, is essentially based on an energy minimization approach, providing fragment states corresponding to various local minima of the fragment-protein interaction potential energy field. Such a procedure is computationally more expeditious than computing the actual physical distributions, but is unable to provide information on entropic effects, essential for free energy estimates.

II. Process

A. Computer Simulation Methods

In aspects of the methods of the present invention, a computer simulation of the interaction between a polypeptide and at least one molecular fragment is conducted, wherein at least one sampling of states from a thermodynamic ensemble representing the polypeptide-fragment system is collected. In aspects of the present invention, the ensemble sampling of the protein-fragment system is obtained through a Metropolis Monte Carlo-type method.

The computer simulation methods of the present invention provide a measure of the of the free energy of binding between the polypeptide and the molecular fragment. One such method is described in U.S. Pat. No. 6,735,530, which is hereby incorporated by reference in its entirety. Modifications to such method that would be readily apparent to one of skill in the art can also be used in the methods of the present invention.

In embodiments, the computer simulation methods of the present invention determine a measure of the chemical potential, defined as $B_{critical}$ ("$B_c$"). $B_c$ is defined as the minimum chemical potential value (referred to as "B" in U.S. Pat. No. 6,735,530) for which a particular fragment is persistently observed in the vicinity of a residue, wherein B is related to the excess chemical potential of the system according to the relation $B = \mu'/kT + \ln\langle N \rangle$, where $\mu'$ is the excess chemical potential, k is Boltzmann's constant, T is the absolute temperature, and $\langle N \rangle$ is the average number of molecular fragments in the simulation.

In further embodiments of the present invention, a particular type of fragment is then considered to be persistently observed in the vicinity of a residue when the average number of fragments in the vicinity of the residue is greater than or equal to 0.8. In a particular aspect of the present invention, a given type of fragment is considered to be persistently observed in the vicinity of a residue when the average number of fragments in the vicinity is greater than or equal to 0.9.

The $B_c$ value that is assigned to any particular fragment-residue pair is an estimate of the fragment's free energy of binding for a binding site on the polypeptide in the vicinity of the considered residue. These affinity values thus attempt to account for both enthalpic and entropic contributions.

Comparing sets of $B_c$ values for different fragment types is valuable to help identify protein binding sites as follows: a binding site is identified as a set of neighboring residues with low $B_c$ values (high affinity) for multiple fragments with diverse physico-chemical properties. This approach is based on the assumption that diverse interactions in a localized region are the necessary condition for ensuring the specificity of a binding site. This numerical localization of binding sites is preferably, but not necessarily, complemented by experimental binding information, such as co-crystal X-ray data, mutational analysis or other approaches known to one skilled in the art.

In embodiments of the present invention, a computer simulation using water as the fragment is conducted and sites that tightly bind the water fragments are eliminated as potential binding sites. Thus, the organic fragments must demonstrate the ability to out-compete water in a particular site in order for that site to be identified as a potential ligand binding site.

Compared to the above described residue-based proximity criteria, more detailed calculations of the binding mode volumes $\Delta V_b$ can be used to provide more accurate estimates of the free energy of binding. Such improved binding mode volume estimates are determined by identifying "clumps" in the fragment distribution. This can be achieved by clustering sampled fragment states belonging to the same potential energy well. For this purpose one makes use of the potential energies saved for the sampled fragment states.

B. Binding Analysis

A first estimate of the binding affinity of a given fragment for different regions on the protein surface can be obtained by assigning a critical chemical potential ($B_c$) to each fragment-residue pair. Such a chemical potential can be calculated from the thermodynamic ensemble data by using the method described in U.S. Pat. No. 6,735,530 in the case of a binding volume $\Delta V_b$ defined for each residue according to the following proximity criteria:

a fragment state is considered to be in proximity of a given residue if at least one fragment-protein atom pair (a, b) is such that $$r_{ab} < \alpha(R_{VdW,a} + R_{VdW,b}),  \quad (33)$$

where $r_{ab}$ is the distance between the two atoms, $R_{VdW}$ is the Van der Waals radius and $\alpha$ is a numerical parameter. In an embodiment, $\alpha$ is between 0.5 and 2.0, and typically chosen to be 1.2. In one aspect the Van der Waals radius is half the Lennard-Jones parameter σ from the considered molecular-mechanics force-field used for the Monte Carlo simulation. In an aspect of the present invention, the molecular mechanics force field is selected from one of the group consisting of MM2, MM3, MM4, OPLS, OPLS-AA, AMBER, GROMOS, CHARMM, Xplor, Discover, MMFF and Tripos and others known by those skilled in the art. AMBER is a particularly preferred force field. (*Reviews in Computational Chemistry, Vol* 16, Lipkowitz and Boyd, eds., John Wiley & Sons, New York, N.Y., 2000).

In another aspect of the present invention, following the computer simulation of the interaction between the polypeptide and at least one fragment type, and the assignment of affinity values to each fragment-residue pair, a binding analysis profile is outputted that comprises a matrix of $B_c$ values for each fragment-residue pair.

In an embodiment of the present invention, numerous separate computer simulations are conducted on a particular polypeptide, wherein in each simulation a different fragment type interacts with the protein. For example, a simulation of polypeptide A is conducted with fragment X, wherein interaction energies are calculated, and affinity values $B_c$ assigned to each fragment-residue pair as described above. A computer simulation of polypeptide A is then conducted with fragment Y, wherein interaction energies are calculated, and affinity values assigned to each fragment-residue pair as described above, etc.

When multiple simulations are conducted for a given polypeptide, a separate affinity value matrix can be generated for each fragment type. In this way the output enables a ranking of the residues with respect to average fragment-binding affinity for a given residue. For example, a matrix of affinity values can be generated which represent averages over various fragment families (for example, polar, aliphatic, heterocyclic, etc.), and the polypeptide surface can then be coded according to these average fragment-residue binding affinities. For visualization purposes, residues with higher and lower fragment binding affinity values can be color-coded accordingly. For example, residues with high average fragment affinity can be displayed in various degrees of red, while the residues with low average fragment affinity are represented in light to dark blue. Other related coloring schemes can be used which are known by those skilled in the art. Such a color-coding of the three-dimensional rendering of the protein provides an efficient way to highlight the high affinity regions, i.e., the potential binding sites, of the protein.

The residue-fragment affinity can also be used to identify key fragments which can be used to design ligands, i.e., potential drug candidates. For one or more selected residues, molecular fragments can be ranked according to their affinity value. For example, for a selected residue, the molecular fragments can be listed in ascending or descending order of their $B_c$ values. Similarly, in an embodiment, the invention allows the display of, for each fragment, a table of residues that highlights the residues on the protein surface for which a particular fragment has the highest affinity. The results presented in such a table can again be visualized by appropriate color-coding of the three-dimensional rendering of the protein.

The fragment-residue affinity values can also be used as a numerical convergence criteria of the Monte Carlo simulation. For example, a matrix of B-critical values derived from all sampling data collected can be saved for each fragment-residue pair (an "affinity profile") at successive intervals along the Monte Carlo simulation. Convergence is considered to be achieved when the affinity profile remains invariant within a consistent range of statistical variation.

The fragment-residue affinity can also be used to measure the extent to which different simulation implementations of the same physical system give statistically the same or different results.

The residue-fragment affinity values can also be used to identify key fragments that can be used to design ligands (i.e. drug candidates). For one or more selected residues, molecular fragments can be ranked according to affinity value. For example, for a selected residue, the molecular fragments can be listed in ascending or descending order of residue-fragment affinity. Similarly, in an embodiment, the invention enables the display of a table of residues for each fragment that highlights the regions on the protein for which the fragment has the highest affinity.

The present invention is described in further detail in the following non-limiting examples.

EXAMPLES

Example 1

The following data in Table 1 was generated from a simulation conducted according to the methods of the present invention on the protein Caspase-3. Amino acid residues are listed on the left hand side, while different fragment types are listed at the top. The binding affinities $B_c$ associated with the fragment-residue pairs are listed.

TABLE 1

Fragment Binding Affinity for Caspase-3

| | acet-amide | acetone | benzene | carboxy-lic acid | dimethyl sulfoxide | ethanol | imida-zole | iso-butane | pyrimi-dine | tetra-hydro-furan | urea | $H_2O$ |
|---|---|---|---|---|---|---|---|---|---|---|---|---|
| ACE A 0 | 0 | 0 | 0 | 0 | 0 | 0 | 0 | 0 | 0 | 0 | 0 | 0 |
| ASN A 35 | 0 | −14.530 | 0 | 0 | −19.171 | 0 | −27.307 | 0 | 0 | −12.976 | −22.528 | 0 |
| SER A 36 | 0 | 0 | 0 | 0 | 0 | 0 | 0 | 0 | 0 | 0 | 0 | 0 |
| TYR A 37 | −21.098 | 0 | −6.808 | 0 | 0 | 0 | −21.307 | 0 | 0 | 0 | −22.528 | 0 |
| LYS A 38 | 0 | 0 | −6.808 | 0 | 0 | 0 | 0 | 0 | 0 | 0 | 0 | 0 |
| MET A 39 | 0 | 0 | 0 | 0 | 0 | 0 | 0 | 0 | 0 | 0 | 0 | 0 |
| ASP A 40 | 0 | 0 | 0 | 0 | 0 | 0 | 0 | 0 | 0 | 0 | 0 | 0 |
| TYR A 41 | 0 | 0 | 0 | 0 | 0 | 0 | 0 | 0 | −12.472 | 0 | 0 | 0 |
| PRO A 42 | 0 | 0 | 0 | 0 | 0 | 0 | 0 | 0 | 0 | 0 | 0 | 0 |
| GLU A 43 | 0 | 0 | 0 | −17.593 | 0 | −18.233 | 0 | 0 | 0 | 0 | −19.528 | −19 |
| MET A 44 | 0 | 0 | 0 | 0 | 0 | 0 | 0 | 0 | 0 | 0 | 0 | 0 |
| GLY A 45 | 0 | 0 | 0 | 0 | 0 | 0 | 0 | 0 | 0 | 0 | 0 | 0 |
| LEU A 46 | 0 | 0 | 0 | 0 | 0 | 0 | 0 | 0 | 0 | 0 | 0 | −18 |

TABLE 1-continued

Fragment Binding Affinity for Caspase-3

| | acet-amide | acetone | benzene | carboxy-lic acid | dimethyl sulfoxide | ethanol | imida-zole | iso-butane | pyrimi-dine | tetra-hydro-furan | urea | H$_2$O |
|---|---|---|---|---|---|---|---|---|---|---|---|---|
| CYS A 47 | 0 | 0 | 0 | 0 | 0 | 0 | 0 | 0 | 0 | 0 | 0 | 0 |
| ILE A 48 | 0 | 0 | 0 | 0 | 0 | 0 | 0 | 0 | 0 | 0 | 0 | 0 |
| ILE A 49 | 0 | 0 | 0 | 0 | 0 | 0 | 0 | 0 | 0 | 0 | 0 | 0 |
| ILE A 50 | 0 | 0 | 0 | 0 | 0 | 0 | 0 | 0 | 0 | 0 | 0 | 0 |
| ASN A 51 | 0 | 0 | 0 | 0 | 0 | 0 | 0 | 0 | 0 | 0 | 0 | 0 |
| ASN A 52 | 0 | 0 | 0 | 0 | 0 | 0 | 0 | 0 | 0 | 0 | 0 | 0 |
| LYS A 53 | 0 | 0 | 0 | 0 | 0 | 0 | 0 | 0 | 0 | 0 | 0 | 0 |
| ASN A 54 | 0 | 0 | 0 | 0 | 0 | 0 | 0 | 0 | 0 | 0 | 0 | 0 |
| PHE A 55 | 0 | 0 | 0 | 0 | 0 | 0 | 0 | 0 | 0 | 0 | 0 | 0 |
| HIE A 56 | 0 | 0 | 0 | 0 | 0 | 0 | 0 | 0 | 0 | 0 | 0 | 0 |
| LYS A 57 | 0 | 0 | 0 | 0 | 0 | 0 | 0 | 0 | 0 | 0 | 0 | 0 |
| SER A 58 | 0 | 0 | 0 | 0 | 0 | 0 | 0 | 0 | 0 | 0 | 0 | 0 |
| THR A 59 | 0 | 0 | 0 | 0 | 0 | 0 | 0 | 0 | 0 | 0 | 0 | 0 |
| GLY A 60 | 0 | 0 | 0 | 0 | 0 | 0 | 0 | 0 | 0 | 0 | 0 | 0 |
| MET A 61 | −31.098 | −14.530 | 0 | −28.593 | −29.171 | −23.233 | −22.307 | 0 | 0 | −13.976 | −30.528 | 0 |
| THR A 62 | 0 | 0 | 0 | 0 | 0 | 0 | 0 | 0 | −11.472 | 0 | 0 | 0 |
| SER A 63 | 0 | 0 | 0 | −12.593 | 0 | 0 | 0 | 0 | −11.472 | 0 | 0 | 0 |
| ARG A 64 | −31.098 | −30.530 | −5.808 | −28.593 | −29.171 | −26.233 | −35.307 | −6.330 | −17.472 | −23.976 | −34.528 | −23 |
| SER A 65 | 0 | 0 | 0 | 0 | 0 | 0 | 0 | 0 | 0 | 0 | 0 | 0 |
| GLY A 66 | 0 | 0 | 0 | 0 | 0 | 0 | 0 | 0 | 0 | 0 | 0 | 0 |
| THR A 67 | 0 | 0 | 0 | 0 | 0 | 0 | 0 | 0 | 0 | 0 | 0 | −15 |
| ASP A 68 | 0 | 0 | 0 | 0 | 0 | 0 | 0 | 0 | 0 | 0 | 0 | 0 |
| VAL A 69 | 0 | 0 | 0 | 0 | 0 | 0 | 0 | 0 | 0 | 0 | 0 | 0 |
| ASP A 70 | 0 | 0 | 0 | 0 | 0 | 0 | 0 | 0 | 0 | 0 | 0 | −15 |
| ALA A 71 | 0 | 0 | 0 | 0 | 0 | 0 | 0 | 0 | 0 | 0 | 0 | 0 |
| ALA A 72 | 0 | 0 | 0 | 0 | 0 | 0 | 0 | 0 | 0 | 0 | 0 | 0 |
| ASN A 73 | 0 | 0 | 0 | 0 | 0 | 0 | 0 | 0 | 0 | 0 | 0 | 0 |
| LEU A 74 | 0 | 0 | 0 | 0 | 0 | 0 | 0 | 0 | 0 | 0 | 0 | 0 |
| ARG A 75 | 0 | 0 | 0 | 0 | 0 | 0 | 0 | 0 | 0 | 0 | 0 | 0 |
| GLU A 76 | 0 | 0 | 0 | 0 | 0 | 0 | 0 | 0 | 0 | 0 | 0 | 0 |
| THR A 77 | 0 | 0 | 0 | 0 | 0 | 0 | 0 | 0 | 0 | 0 | 0 | 0 |
| PHE A 78 | 0 | 0 | 0 | 0 | 0 | 0 | 0 | 0 | 0 | 0 | 0 | 0 |
| ARG A 79 | 0 | 0 | 0 | 0 | 0 | 0 | 0 | 0 | 0 | 0 | 0 | 0 |
| ASN A 80 | 0 | 0 | 0 | 0 | 0 | 0 | 0 | 0 | 0 | 0 | 0 | 0 |
| LEU A 81 | 0 | 0 | 0 | 0 | 0 | 0 | 0 | 0 | 0 | 0 | 0 | 0 |
| LYS A 82 | 0 | 0 | 0 | 0 | 0 | 0 | 0 | 0 | 0 | 0 | 0 | 0 |
| TYR A 83 | 0 | 0 | 0 | 0 | 0 | 0 | 0 | 0 | 0 | 0 | 0 | 0 |
| GLU A 84 | 0 | 0 | 0 | −12.593 | 0 | 0 | 0 | 0 | 0 | 0 | 0 | −18 |
| VAL A 85 | 0 | 0 | 0 | 0 | 0 | 0 | 0 | 0 | 0 | 0 | 0 | 0 |
| ARG A 86 | 0 | 0 | 0 | 0 | 0 | 0 | 0 | 0 | −10.472 | 0 | 0 | 0 |
| ASN A 87 | 0 | 0 | 0 | 0 | 0 | 0 | 0 | 0 | 0 | 0 | 0 | 0 |
| LYS A 88 | −27.098 | −16.530 | 0 | 0 | −21.171 | 0 | −30.307 | 0 | −12.472 | −12.976 | −26.528 | 0 |
| ASN A 89 | 0 | 0 | 0 | 0 | −16.171 | 0 | 0 | 0 | −12.472 | 0 | 0 | 0 |
| ASP A 90 | 0 | 0 | 0 | 0 | 0 | 0 | 0 | 0 | 0 | 0 | 0 | 0 |
| LEU A 91 | −27.098 | −15.530 | 0 | 0 | −17.171 | 0 | −30.307 | 0 | 0 | −11.976 | −26.528 | 0 |
| THR A 92 | 0 | 0 | 0 | 0 | 0 | 0 | 0 | 0 | 0 | 0 | 0 | 0 |
| ARG A 93 | 0 | 0 | 0 | 0 | 0 | 0 | 0 | 0 | −9.472 | 0 | 0 | 0 |
| GLU A 94 | 0 | 0 | 0 | −15.593 | −16.171 | −13.233 | 0 | 0 | 0 | 0 | 0 | 0 |
| GLU A 95 | −27.098 | −16.530 | 0 | 0 | −21.171 | 0 | −30.307 | 0 | 0 | −12.976 | −26.528 | 0 |
| ILE A 96 | 0 | 0 | 0 | 0 | 0 | 0 | 0 | 0 | 0 | 0 | 0 | 0 |
| VAL A 97 | −18.098 | −17.530 | 0 | 0 | −24.171 | 0 | 0 | 0 | 0 | 0 | −17.528 | 0 |
| GLU A 98 | −22.098 | −13.530 | 0 | −21.593 | −17.171 | 0 | −23.307 | 0 | 0 | 0 | −25.528 | −27 |
| LEU A 99 | 0 | 0 | 0 | 0 | −16.171 | 0 | −23.307 | 0 | −10.472 | 0 | 0 | 0 |
| MET A 100 | 0 | 0 | 0 | 0 | 0 | 0 | 0 | 0 | 0 | 0 | 0 | 0 |
| ARG A 101 | −18.098 | −17.530 | 0 | −15.593 | −24.171 | −23.233 | 0 | 0 | 0 | −9.976 | −25.528 | −27 |
| ASP A 102 | −21.098 | 0 | 0 | −21.593 | 0 | −23.233 | −30.307 | 0 | 0 | 0 | −25.528 | −27 |
| VAL A 103 | 0 | 0 | 0 | 0 | 0 | 0 | 0 | 0 | 0 | 0 | 0 | 0 |
| SER A 104 | 0 | −16.530 | 0 | 0 | −18.171 | 0 | −24.307 | 0 | −10.472 | −14.976 | 0 | 0 |
| LYS A 105 | −22.098 | −16.530 | 0 | −21.593 | −18.171 | −23.233 | −30.307 | 0 | −10.472 | −14.976 | −25.528 | −27 |
| GLU A 106 | −21.098 | −14.530 | 0 | 0 | −18.171 | −12.233 | −24.307 | 0 | −10.472 | −14.976 | 0 | 0 |
| ASP A 107 | 0 | −16.530 | −5.808 | −16.593 | −18.171 | −18.233 | −24.307 | 0 | 0 | −14.976 | −19.528 | 0 |
| HIE A 108 | 0 | 0 | 0 | 0 | 0 | 0 | 0 | 0 | 0 | 0 | 0 | 0 |
| SER A 109 | 0 | 0 | 0 | 0 | 0 | 0 | 0 | 0 | 0 | 0 | 0 | 0 |
| LYS A 110 | 0 | 0 | 0 | −17.593 | 0 | −18.233 | 0 | 0 | 0 | 0 | −19.528 | −17 |
| ARG A 111 | 0 | 0 | 0 | −17.593 | 0 | −18.233 | 0 | 0 | 0 | 0 | −19.528 | −19 |
| SER A 112 | 0 | 0 | 0 | 0 | 0 | 0 | 0 | 0 | 0 | 0 | 0 | 0 |
| SER A 113 | 0 | 0 | 0 | 0 | 0 | 0 | 0 | 0 | 0 | 0 | 0 | 0 |
| PHE A 114 | 0 | 0 | 0 | 0 | 0 | 0 | 0 | 0 | 0 | 0 | 0 | 0 |
| VAL A 115 | 0 | 0 | 0 | 0 | 0 | 0 | 0 | 0 | 0 | 0 | 0 | 0 |
| CYS A 116 | 0 | 0 | 0 | 0 | 0 | 0 | 0 | 0 | 0 | 0 | 0 | 0 |
| VAL A 117 | 0 | 0 | 0 | 0 | 0 | 0 | 0 | 0 | 0 | 0 | 0 | 0 |
| LEU A 118 | 0 | 0 | 0 | 0 | 0 | 0 | 0 | 0 | 0 | 0 | 0 | 0 |
| LEU A 119 | 0 | 0 | 0 | 0 | 0 | 0 | 0 | 0 | 0 | 0 | 0 | −15 |

TABLE 1-continued

Fragment Binding Affinity for Caspase-3

| | acet-amide | acetone | benzene | carboxy-lic acid | dimethyl sulfoxide | ethanol | imida-zole | iso-butane | pyrimi-dine | tetra-hydro-furan | urea | H₂O |
|---|---|---|---|---|---|---|---|---|---|---|---|---|
| SER A 120 | −26.098 | −14.530 | −5.808 | −28.593 | −27.171 | −26.233 | −35.307 | −6.330 | −17.472 | −23.976 | −34.528 | −23 |
| HIP A 121 | −31.098 | −20.530 | −5.808 | −28.593 | −29.171 | −23.233 | −35.307 | −6.330 | −17.472 | −23.976 | −30.528 | −26 |
| GLY A 122 | −31.098 | −20.530 | 0 | −28.593 | −29.171 | −23.233 | −22.307 | 0 | −14.472 | −14.976 | −30.528 | −20 |
| GLU A 123 | 0 | −19.530 | 0 | 0 | −23.171 | 0 | 0 | 0 | 0 | 0 | 0 | 0 |
| GLU A 124 | 0 | 0 | 0 | 0 | 0 | 0 | 0 | 0 | −13.472 | 0 | 0 | 0 |
| GLY A 125 | 0 | 0 | 0 | 0 | 0 | 0 | 0 | 0 | 0 | 0 | 0 | 0 |
| ILE A 126 | 0 | 0 | 0 | 0 | 0 | 0 | 0 | 0 | 0 | 0 | 0 | 0 |
| ILE A 127 | 0 | 0 | 0 | 0 | 0 | 0 | 0 | 0 | 0 | 0 | 0 | 0 |
| PHE A 128 | 0 | −19.530 | 0 | 0 | −29.171 | 0 | 0 | 0 | 0 | 0 | 0 | 0 |
| GLY A 129 | 0 | 0 | 0 | 0 | 0 | 0 | 0 | 0 | 0 | 0 | 0 | 0 |
| THR A 130 | 0 | 0 | 0 | 0 | 0 | 0 | 0 | 0 | 0 | 0 | 0 | 0 |
| ASN A 131 | 0 | 0 | 0 | 0 | 0 | 0 | 0 | 0 | 0 | 0 | 0 | 0 |
| GLY A 132 | 0 | 0 | 0 | 0 | 0 | 0 | 0 | 0 | 0 | 0 | 0 | 0 |
| PRO A 133 | 0 | 0 | 0 | 0 | 0 | 0 | 0 | 0 | −9.472 | 0 | 0 | 0 |
| VAL A 134 | 0 | 0 | 0 | 0 | 0 | 0 | 0 | 0 | −9.472 | 0 | 0 | 0 |
| ASP A 135 | 0 | 0 | 0 | 0 | 0 | 0 | 0 | 0 | −9.472 | 0 | 0 | 0 |
| LEU A 136 | 0 | 0 | 0 | 0 | 0 | 0 | 0 | 0 | 0 | 0 | 0 | 0 |
| LYS A 137 | 0 | 0 | −7.808 | −13.593 | 0 | −11.233 | −25.307 | 0 | 0 | 0 | −23.528 | −21 |
| LYS A 138 | −18.098 | −17.530 | −5.808 | 0 | −24.171 | 0 | 0 | 0 | 0 | −9.976 | −17.528 | 0 |
| ILE A 139 | 0 | 0 | 0 | 0 | 0 | 0 | 0 | 0 | 0 | 0 | 0 | 0 |
| THR A 140 | 0 | 0 | 0 | 0 | 0 | 0 | 0 | 0 | 0 | 0 | 0 | 0 |
| ASN A 141 | 0 | 0 | −5.808 | 0 | −16.171 | 0 | −25.307 | 0 | 0 | 0 | −23.528 | 0 |
| PHE A 142 | 0 | 0 | −5.808 | 0 | 0 | 0 | 0 | 0 | 0 | 0 | 0 | 0 |
| PHE A 143 | 0 | 0 | 0 | 0 | 0 | 0 | 0 | 0 | 0 | 0 | 0 | 0 |
| ARG A 144 | −24.098 | −13.530 | −5.808 | 0 | −16.171 | −15.233 | −21.307 | 0 | 0 | −9.976 | −18.528 | −18 |
| GLY A 145 | 0 | 0 | 0 | 0 | 0 | 0 | 0 | 0 | 0 | 0 | 0 | 0 |
| ASP A 146 | 0 | 0 | 0 | −14.593 | 0 | −13.233 | 0 | 0 | 0 | 0 | 0 | 0 |
| ARG A 147 | 0 | −13.530 | −5.808 | −14.593 | −16.171 | −13.233 | 0 | 0 | 0 | 0 | 0 | 0 |
| CYS A 148 | 0 | 0 | 0 | 0 | −18.171 | −12.233 | −24.307 | 0 | 0 | −14.976 | 0 | 0 |
| ARG A 149 | −21.098 | −16.530 | 0 | 0 | −18.171 | −12.233 | −24.307 | 0 | −10.472 | −14.976 | 0 | 0 |
| SER A 150 | −21.098 | −16.530 | 0 | 0 | −18.171 | −12.233 | −24.307 | 0 | −10.472 | −14.976 | 0 | 0 |
| LEU A 151 | 0 | 0 | 0 | 0 | 0 | 0 | 0 | 0 | 0 | 0 | 0 | 0 |
| THR A 152 | 0 | 0 | 0 | 0 | 0 | 0 | 0 | 0 | 0 | 0 | 0 | −19 |
| GLY A 153 | −21.098 | 0 | −6.808 | 0 | 0 | −12.233 | −22.307 | 0 | −13.472 | −11.976 | −22.528 | −19 |
| LYS A 154 | 0 | 0 | 0 | 0 | 0 | 0 | 0 | 0 | 0 | 0 | 0 | 0 |
| PRO A 155 | 0 | 0 | 0 | 0 | 0 | 0 | 0 | 0 | 0 | 0 | 0 | 0 |
| LYS A 156 | 0 | 0 | 0 | 0 | 0 | 0 | 0 | 0 | 0 | 0 | 0 | −19 |
| LEU A 157 | 0 | 0 | 0 | 0 | 0 | 0 | 0 | 0 | 0 | 0 | 0 | 0 |
| PHE A 158 | 0 | 0 | 0 | 0 | 0 | 0 | 0 | 0 | 0 | 0 | 0 | 0 |
| ILE A 159 | 0 | 0 | 0 | 0 | 0 | 0 | 0 | 0 | 0 | 0 | 0 | 0 |
| ILE A 160 | 0 | 0 | 0 | 0 | 0 | 0 | 0 | 0 | 0 | 0 | 0 | 0 |
| GLN A 161 | −26.098 | −13.530 | −5.808 | 0 | −16.171 | 0 | −29.307 | −6.330 | 0 | −23.976 | −26.528 | −15 |
| ALA A 162 | −31.098 | −30.530 | −5.808 | −28.593 | −29.171 | −26.233 | −29.307 | −6.330 | 0 | −23.976 | −34.528 | 0 |
| CYM A 163 | −31.098 | −30.530 | −5.808 | −28.593 | −29.171 | −23.233 | −35.307 | −6.330 | −17.472 | −23.976 | −34.528 | −26 |
| ARG A 164 | 0 | 0 | 0 | 0 | 0 | 0 | 0 | 0 | −14.472 | 0 | 0 | 0 |
| GLY A 165 | 0 | 0 | 0 | 0 | 0 | 0 | 0 | 0 | 0 | 0 | 0 | 0 |
| THR A 166 | 0 | 0 | 0 | 0 | 0 | 0 | 0 | 0 | 0 | 0 | 0 | 0 |
| GLU A 167 | −26.098 | −16.530 | 0 | 0 | −25.171 | 0 | −30.307 | 0 | −10.472 | −10.976 | −25.528 | 0 |
| LEU A 168 | 0 | 0 | 0 | 0 | −25.171 | 0 | 0 | 0 | 0 | −10.976 | 0 | 0 |
| ASP A 169 | 0 | 0 | 0 | 0 | 0 | 0 | 0 | 0 | 0 | 0 | 0 | 0 |
| CYS A 170 | 0 | 0 | 0 | 0 | 0 | 0 | 0 | 0 | 0 | 0 | 0 | 0 |
| GLY A 171 | 0 | 0 | 0 | 0 | 0 | 0 | 0 | 0 | 0 | 0 | 0 | 0 |
| ILE A 172 | 0 | 0 | 0 | 0 | 0 | 0 | 0 | 0 | 0 | 0 | 0 | 0 |
| GLU A 173 | 0 | 0 | 0 | 0 | 0 | 0 | 0 | 0 | 0 | 0 | 0 | 0 |
| NME A 999 | 0 | 0 | 0 | 0 | 0 | 0 | 0 | 0 | 0 | 0 | 0 | 0 |
| ACE E 0 | 0 | 0 | 0 | 0 | 0 | 0 | 0 | 0 | 0 | 0 | 0 | 0 |
| HID E 185 | 0 | −15.530 | 0 | −19.593 | −18.171 | 0 | −19.307 | 0 | 0 | 0 | −18.528 | −16 |
| LYS E 186 | 0 | 0 | 0 | −15.593 | −18.171 | −12.233 | 0 | 0 | 0 | 0 | 0 | −16 |
| ILE E 187 | −21.098 | −15.530 | 0 | 0 | −20.171 | 0 | −22.307 | 0 | −13.472 | −11.976 | −23.528 | 0 |
| PRO E 188 | 0 | 0 | 0 | 0 | 0 | 0 | 0 | 0 | 0 | 0 | 0 | 0 |
| VAL E 189 | 0 | 0 | −5.808 | 0 | 0 | 0 | 0 | 0 | 0 | 0 | 0 | 0 |
| ASP E 190 | 0 | 0 | −7.808 | 0 | 0 | −11.233 | 0 | 0 | 0 | 0 | 0 | 0 |
| ALA E 191 | 0 | 0 | 0 | 0 | 0 | 0 | 0 | 0 | 0 | 0 | 0 | −19 |
| ASP E 192 | −21.098 | 0 | 0 | 0 | 0 | 0 | −21.307 | 0 | −13.472 | 0 | −22.528 | −19 |
| PHE E 193 | 0 | 0 | 0 | 0 | 0 | 0 | 0 | 0 | 0 | 0 | 0 | 0 |
| LEU E 194 | 0 | 0 | 0 | 0 | 0 | 0 | 0 | 0 | 0 | 0 | 0 | 0 |
| TYR E 195 | 0 | 0 | −7.808 | 0 | 0 | −11.233 | 0 | 0 | 0 | 0 | 0 | 0 |
| ALA E 196 | 0 | 0 | 0 | 0 | 0 | 0 | 0 | 0 | 0 | 0 | 0 | 0 |
| TYR E 197 | 0 | 0 | 0 | 0 | 0 | 0 | 0 | 0 | 0 | 0 | 0 | 0 |
| SER E 198 | 0 | 0 | 0 | 0 | 0 | 0 | 0 | 0 | 0 | 0 | 0 | 0 |
| THR E 199 | 0 | 0 | 0 | 0 | 0 | 0 | 0 | 0 | 0 | 0 | 0 | 0 |
| ALA E 200 | 0 | 0 | 0 | 0 | 0 | 0 | 0 | 0 | 0 | 0 | 0 | 0 |
| PRO E 201 | 0 | 0 | 0 | 0 | 0 | 0 | 0 | 0 | −14.472 | 0 | 0 | 0 |

TABLE 1-continued

Fragment Binding Affinity for Caspase-3

| | acet-amide | acetone | benzene | carboxy-lic acid | dimethyl sulfoxide | ethanol | imida-zole | iso-butane | pyrimi-dine | tetra-hydro-furan | urea | H$_2$O |
|---|---|---|---|---|---|---|---|---|---|---|---|---|
| GLY E 202 | 0 | 0 | 0 | 0 | 0 | 0 | 0 | 0 | 0 | 0 | 0 | 0 |
| TYR E 203 | 0 | 0 | 0 | 0 | 0 | 0 | 0 | 0 | 0 | −9.976 | 0 | 0 |
| TYR E 204 | 0 | 0 | 0 | −12.593 | −29.171 | 0 | 0 | 0 | −11.472 | −12.976 | 0 | 0 |
| SER E 205 | −31.098 | −30.530 | 0 | −28.593 | −29.171 | −26.233 | −35.307 | −6.330 | −17.472 | −23.976 | −34.528 | −23 |
| TRP E 206 | −26.098 | 0 | 0 | 0 | 0 | 0 | 0 | −6.330 | −11.472 | 0 | −26.528 | 0 |
| ARG E 207 | −31.098 | −30.530 | −5.808 | −28.593 | −29.171 | −26.233 | −35.307 | −6.330 | −17.472 | −23.976 | −34.528 | −15 |
| ASN E 208 | 0 | 0 | 0 | 0 | 0 | 0 | 0 | 0 | 0 | −9.976 | 0 | 0 |
| SER E 209 | 0 | 0 | 0 | 0 | 0 | 0 | 0 | 0 | 0 | 0 | 0 | 0 |
| LYS E 210 | 0 | 0 | 0 | −13.593 | 0 | 0 | 0 | 0 | 0 | 0 | 0 | 0 |
| ASP E 211 | 0 | 0 | 0 | −13.593 | 0 | 0 | 0 | 0 | 0 | 0 | 0 | 0 |
| GLY E 212 | 0 | 0 | 0 | 0 | 0 | 0 | 0 | 0 | 0 | 0 | 0 | 0 |
| SER E 213 | 0 | 0 | 0 | 0 | 0 | 0 | 0 | 0 | 0 | 0 | 0 | 0 |
| TRP E 214 | 0 | 0 | 0 | 0 | 0 | 0 | 0 | 0 | 0 | −9.976 | 0 | 0 |
| PHE E 215 | 0 | 0 | 0 | 0 | 0 | 0 | 0 | 0 | 0 | 0 | 0 | 0 |
| ILE E 216 | 0 | 0 | 0 | 0 | 0 | 0 | 0 | 0 | 0 | 0 | 0 | 0 |
| GLN E 217 | 0 | 0 | 0 | 0 | 0 | 0 | 0 | 0 | 0 | 0 | 0 | 0 |
| SER E 218 | 0 | 0 | 0 | 0 | 0 | 0 | 0 | 0 | 0 | 0 | 0 | 0 |
| LEU E 219 | 0 | 0 | 0 | 0 | 0 | 0 | 0 | 0 | 0 | 0 | 0 | 0 |
| CYS E 220 | 0 | 0 | 0 | 0 | 0 | 0 | 0 | 0 | 0 | 0 | 0 | 0 |
| ALA E 221 | 0 | 0 | 0 | 0 | 0 | 0 | 0 | 0 | 0 | 0 | 0 | 0 |
| MET E 222 | 0 | 0 | 0 | 0 | 0 | 0 | 0 | 0 | 0 | 0 | 0 | 0 |
| LEU E 223 | 0 | 0 | 0 | 0 | 0 | 0 | 0 | 0 | 0 | 0 | 0 | 0 |
| LYS E 224 | 0 | 0 | 0 | 0 | 0 | 0 | 0 | 0 | 0 | 0 | 0 | 0 |
| GLN E 225 | 0 | 0 | 0 | 0 | 0 | 0 | −29.307 | 0 | −11.472 | 0 | 0 | −18 |
| TYR E 226 | 0 | 0 | 0 | 0 | 0 | 0 | −29.307 | 0 | −11.472 | 0 | 0 | −18 |
| ALA E 227 | 0 | 0 | 0 | 0 | 0 | 0 | 0 | 0 | 0 | 0 | 0 | 0 |
| ASP E 228 | 0 | 0 | 0 | 0 | 0 | 0 | −29.307 | 0 | −11.472 | 0 | 0 | −18 |
| LYS E 229 | 0 | 0 | 0 | 0 | 0 | 0 | −29.307 | 0 | −12.472 | 0 | 0 | −18 |
| LEU E 230 | −18.098 | −13.530 | 0 | −16.593 | −17.171 | −15.233 | −21.307 | 0 | −12.472 | 0 | −20.528 | −16 |
| GLU E 231 | 0 | 0 | 0 | 0 | 0 | 0 | 0 | 0 | 0 | 0 | 0 | 0 |
| PHE E 232 | 0 | 0 | 0 | 0 | 0 | 0 | 0 | 0 | 0 | 0 | 0 | 0 |
| MET E 233 | 0 | 0 | 0 | 0 | 0 | 0 | 0 | 0 | 0 | 0 | 0 | 0 |
| HIE E 234 | 0 | 0 | 0 | −16.593 | 0 | 0 | 0 | 0 | 0 | 0 | 0 | −26 |
| ILE E 235 | 0 | 0 | 0 | 0 | 0 | 0 | 0 | 0 | 0 | 0 | 0 | 0 |
| LEU E 236 | 0 | 0 | 0 | 0 | 0 | 0 | 0 | 0 | 0 | 0 | 0 | 0 |
| THR E 237 | 0 | 0 | 0 | 0 | 0 | 0 | 0 | 0 | 0 | 0 | 0 | 0 |
| ARG E 238 | −18.098 | −13.530 | 0 | −16.593 | −17.171 | −15.233 | −22.307 | 0 | −12.472 | −9.976 | −20.528 | −26 |
| VAL E 239 | 0 | 0 | 0 | 0 | 0 | 0 | 0 | 0 | 0 | 0 | 0 | 0 |
| ASN E 240 | 0 | 0 | 0 | 0 | 0 | 0 | 0 | 0 | 0 | 0 | 0 | 0 |
| ARG E 241 | −22.098 | −16.530 | −5.808 | 0 | −20.171 | 0 | −24.307 | −4.330 | −12.472 | −15.976 | −19.528 | −23 |
| LYS E 242 | −18.098 | 0 | 0 | 0 | 0 | 0 | −24.307 | 0 | −9.472 | 0 | −19.528 | 0 |
| VAL E 243 | 0 | 0 | 0 | 0 | 0 | 0 | 0 | 0 | 0 | 0 | 0 | 0 |
| ALA E 244 | 0 | 0 | 0 | 0 | 0 | 0 | 0 | 0 | 0 | 0 | 0 | 0 |
| THR E 245 | 0 | −15.530 | 0 | −16.593 | −20.171 | 0 | 0 | −4.330 | −11.472 | −15.976 | 0 | 0 |
| GLU E 246 | −22.098 | −16.530 | 0 | 0 | −19.171 | 0 | −24.307 | 0 | −12.472 | 0 | −19.528 | 0 |
| PHE E 247 | 0 | 0 | 0 | 0 | 0 | 0 | 0 | 0 | 0 | 0 | 0 | 0 |
| GLU E 248 | 0 | 0 | 0 | −16.593 | 0 | 0 | 0 | 0 | 0 | −9.976 | 0 | 0 |
| SER E 249 | 0 | 0 | 0 | 0 | 0 | 0 | 0 | 0 | 0 | −9.976 | 0 | 0 |
| PHE E 250 | 0 | 0 | 0 | 0 | 0 | 0 | 0 | 0 | 0 | 0 | 0 | 0 |
| SER E 251 | 0 | 0 | 0 | 0 | 0 | 0 | 0 | 0 | 0 | 0 | 0 | 0 |
| PHE E 252 | 0 | 0 | 0 | 0 | 0 | 0 | 0 | 0 | 0 | 0 | 0 | 0 |
| ASP E 253 | 0 | 0 | 0 | 0 | 0 | 0 | 0 | 0 | 0 | 0 | 0 | 0 |
| ALA E 254 | 0 | 0 | 0 | 0 | 0 | 0 | 0 | 0 | 0 | 0 | 0 | 0 |
| THR E 255 | 0 | 0 | 0 | 0 | 0 | 0 | 0 | 0 | 0 | 0 | 0 | 0 |
| PHE E 256 | 0 | 0 | 0 | 0 | 0 | 0 | 0 | 0 | 0 | 0 | 0 | 0 |
| HIE E 257 | 0 | 0 | 0 | 0 | 0 | 0 | 0 | 0 | 0 | 0 | 0 | 0 |
| ALA E 258 | 0 | 0 | 0 | 0 | 0 | 0 | 0 | 0 | 0 | 0 | 0 | 0 |
| LYS E 259 | 0 | 0 | 0 | 0 | 0 | 0 | 0 | 0 | 0 | 0 | 0 | 0 |
| LYS E 260 | 0 | 0 | 0 | −16.593 | 0 | 0 | 0 | 0 | 0 | 0 | 0 | 0 |
| GLN E 261 | 0 | 0 | 0 | 0 | 0 | 0 | 0 | 0 | 0 | 0 | 0 | 0 |
| ILE E 262 | 0 | 0 | 0 | 0 | 0 | 0 | 0 | 0 | 0 | 0 | 0 | 0 |
| PRO E 263 | 0 | 0 | 0 | 0 | 0 | 0 | 0 | 0 | 0 | 0 | 0 | 0 |
| CYS E 264 | 0 | 0 | 0 | 0 | 0 | 0 | 0 | 0 | 0 | 0 | 0 | 0 |
| ILE E 265 | 0 | 0 | 0 | 0 | 0 | 0 | 0 | 0 | 0 | 0 | 0 | 0 |
| VAL E 266 | 0 | 0 | 0 | 0 | 0 | 0 | 0 | 0 | 0 | 0 | 0 | 0 |
| SER E 267 | 0 | 0 | 0 | 0 | 0 | 0 | 0 | 0 | 0 | 0 | 0 | 0 |
| MET E 268 | 0 | 0 | −7.808 | 0 | 0 | −11.233 | 0 | 0 | 0 | 0 | 0 | 0 |
| LEU E 269 | 0 | 0 | 0 | 0 | 0 | 0 | 0 | 0 | 0 | 0 | 0 | 0 |
| THR E 270 | −21.098 | 0 | −6.808 | 0 | 0 | 0 | −21.307 | 0 | −13.472 | 0 | −22.528 | 0 |
| LYS E 271 | −21.098 | −15.530 | −6.808 | 0 | −20.171 | −12.233 | −22.307 | 0 | −13.472 | −11.976 | −22.528 | 0 |
| GLU E 272 | −25.098 | −18.530 | 0 | −19.593 | −23.171 | −22.233 | −27.307 | 0 | −13.472 | −12.976 | −22.528 | −21 |
| LEU E 273 | 0 | 0 | 0 | 0 | 0 | 0 | 0 | 0 | 0 | 0 | 0 | 0 |
| TYR E 274 | 0 | 0 | 0 | 0 | 0 | 0 | 0 | 0 | 0 | 0 | 0 | 0 |

TABLE 1-continued

Fragment Binding Affinity for Caspase-3

| | acet-amide | acetone | benzene | carboxy-lic acid | dimethyl sulfoxide | ethanol | imida-zole | iso-butane | pyrimi-dine | tetra-hydro-furan | urea | H₂O |
|---|---|---|---|---|---|---|---|---|---|---|---|---|
| PHE E 275 | 0 | 0 | 0 | 0 | 0 | 0 | 0 | 0 | 0 | 0 | 0 | 0 |
| TYR E 276 | 0 | 0 | 0 | 0 | 0 | 0 | 0 | −4.330 | 0 | 0 | 0 | 0 |
| HIE E 277 | 0 | 0 | 0 | 0 | 0 | 0 | 0 | −4.330 | 0 | 0 | 0 | 0 |
| NME E 999 | 0 | 0 | 0 | 0 | 0 | 0 | 0 | 0 | 0 | 0 | 0 | 0 |
| ACE B 0 | −18.098 | −13.530 | 0 | −16.593 | −17.171 | −15.233 | −21.307 | 0 | −12.472 | 0 | −20.528 | −16 |
| ASN B 35 | 0 | 0 | 0 | 0 | 0 | 0 | 0 | 0 | 0 | 0 | 0 | −23 |
| SER B 36 | 0 | 0 | 0 | 0 | 0 | 0 | 0 | 0 | 0 | 0 | 0 | 0 |
| TYR B 37 | −23.098 | 0 | 0 | 0 | 0 | 0 | −27.307 | 0 | 0 | 0 | 0 | 0 |
| LYS B 38 | 0 | 0 | 0 | 0 | 0 | 0 | 0 | 0 | 0 | 0 | 0 | 0 |
| MET B 39 | 0 | 0 | 0 | 0 | 0 | 0 | 0 | 0 | 0 | 0 | 0 | 0 |
| ASP B 40 | 0 | 0 | 0 | 0 | 0 | 0 | 0 | 0 | 0 | 0 | 0 | 0 |
| TYR B 41 | 0 | 0 | 0 | 0 | 0 | 0 | 0 | 0 | 0 | 0 | 0 | 0 |
| PRO B 42 | 0 | 0 | 0 | 0 | 0 | 0 | 0 | 0 | 0 | 0 | 0 | 0 |
| GLU B 43 | 0 | 0 | 0 | 0 | 0 | 0 | −22.307 | 0 | 0 | 0 | 0 | −17 |
| MET B 44 | 0 | 0 | 0 | 0 | 0 | 0 | 0 | 0 | 0 | 0 | 0 | 0 |
| GLY B 45 | 0 | 0 | 0 | 0 | 0 | 0 | 0 | 0 | 0 | 0 | 0 | −17 |
| LEU B 46 | 0 | 0 | 0 | 0 | 0 | 0 | 0 | 0 | 0 | 0 | 0 | 0 |
| CYS B 47 | 0 | 0 | 0 | 0 | 0 | 0 | 0 | 0 | 0 | 0 | 0 | 0 |
| ILE B 48 | 0 | 0 | 0 | 0 | 0 | 0 | 0 | 0 | 0 | 0 | 0 | 0 |
| ILE B 49 | 0 | 0 | 0 | 0 | 0 | 0 | 0 | 0 | 0 | 0 | 0 | 0 |
| ILE B 50 | 0 | 0 | 0 | 0 | 0 | 0 | 0 | 0 | 0 | 0 | 0 | 0 |
| ASN B 51 | 0 | 0 | 0 | 0 | 0 | 0 | 0 | 0 | 0 | 0 | 0 | 0 |
| ASN B 52 | 0 | 0 | 0 | 0 | 0 | 0 | 0 | 0 | 0 | 0 | 0 | 0 |
| LYS B 53 | −22.098 | 0 | 0 | −15.593 | −20.171 | −14.233 | 0 | 0 | 0 | −11.976 | −17.528 | 0 |
| ASN B 54 | 0 | 0 | 0 | 0 | 0 | −11.233 | 0 | 0 | 0 | 0 | 0 | 0 |
| PHE B 55 | 0 | 0 | 0 | 0 | 0 | 0 | 0 | 0 | 0 | 0 | 0 | 0 |
| HIE B 56 | 0 | 0 | 0 | 0 | 0 | 0 | 0 | 0 | 0 | 0 | 0 | 0 |
| LYS B 57 | 0 | 0 | 0 | 0 | 0 | 0 | 0 | 0 | 0 | 0 | 0 | 0 |
| SER B 58 | 0 | 0 | 0 | 0 | 0 | 0 | 0 | 0 | 0 | 0 | 0 | 0 |
| THR B 59 | 0 | 0 | 0 | 0 | 0 | 0 | 0 | 0 | 0 | 0 | 0 | 0 |
| GLY B 60 | 0 | 0 | 0 | 0 | 0 | 0 | 0 | 0 | 0 | 0 | 0 | 0 |
| MET B 61 | −27.098 | 0 | 0 | 0 | −29.171 | −22.233 | −31.307 | −4.330 | −16.472 | −19.976 | 0 | 0 |
| THR B 62 | 0 | 0 | 0 | 0 | 0 | 0 | 0 | 0 | −12.472 | 0 | 0 | 0 |
| SER B 63 | 0 | 0 | 0 | 0 | 0 | −11.233 | 0 | 0 | 0 | 0 | 0 | 0 |
| ARG B 64 | −27.098 | −16.530 | 0 | −21.593 | −29.171 | −18.233 | −35.307 | −4.330 | −29.472 | −19.976 | −34.528 | −21 |
| SER B 65 | −22.098 | 0 | 0 | −15.593 | −20.171 | −14.233 | 0 | 0 | 0 | −11.976 | −17.528 | 0 |
| GLY B 66 | −22.098 | 0 | 0 | −15.593 | −20.171 | −14.233 | 0 | 0 | 0 | −11.976 | −17.528 | 0 |
| THR B 67 | 0 | 0 | 0 | 0 | 0 | 0 | 0 | 0 | 0 | 0 | 0 | 0 |
| ASP B 68 | −22.098 | 0 | 0 | −15.593 | −20.171 | −14.233 | 0 | 0 | 0 | −11.976 | −17.528 | 0 |
| VAL B 69 | 0 | 0 | 0 | 0 | 0 | 0 | 0 | 0 | 0 | 0 | 0 | 0 |
| ASP B 70 | 0 | 0 | 0 | 0 | 0 | 0 | 0 | 0 | 0 | 0 | 0 | 0 |
| ALA B 71 | 0 | 0 | 0 | 0 | 0 | 0 | 0 | 0 | 0 | 0 | 0 | 0 |
| ALA B 72 | 0 | 0 | 0 | 0 | 0 | 0 | 0 | 0 | 0 | 0 | 0 | 0 |
| ASN B 73 | 0 | 0 | 0 | 0 | 0 | 0 | 0 | 0 | 0 | 0 | 0 | 0 |
| LEU B 74 | 0 | 0 | 0 | 0 | 0 | 0 | 0 | 0 | 0 | 0 | 0 | 0 |
| ARG B 75 | 0 | 0 | 0 | 0 | 0 | 0 | 0 | 0 | 0 | 0 | 0 | 0 |
| GLU B 76 | 0 | 0 | 0 | 0 | 0 | 0 | 0 | 0 | 0 | 0 | 0 | 0 |
| THR B 77 | 0 | 0 | 0 | 0 | 0 | 0 | 0 | 0 | 0 | 0 | 0 | 0 |
| PHE B 78 | 0 | 0 | 0 | 0 | 0 | 0 | 0 | 0 | 0 | 0 | 0 | 0 |
| ARG B 79 | 0 | 0 | 0 | 0 | 0 | 0 | 0 | 0 | 0 | 0 | 0 | 0 |
| ASN B 80 | 0 | 0 | 0 | 0 | 0 | 0 | 0 | 0 | 0 | 0 | 0 | 0 |
| LEU B 81 | 0 | 0 | 0 | 0 | 0 | 0 | 0 | 0 | 0 | 0 | 0 | 0 |
| LYS B 82 | 0 | 0 | 0 | 0 | 0 | 0 | 0 | 0 | 0 | 0 | 0 | 0 |
| TYR B 83 | 0 | 0 | 0 | 0 | 0 | 0 | 0 | 0 | 0 | 0 | 0 | 0 |
| GLU B 84 | 0 | 0 | 0 | 0 | 0 | 0 | 0 | 0 | 0 | 0 | 0 | −17 |
| VAL B 85 | 0 | 0 | 0 | 0 | 0 | 0 | 0 | 0 | 0 | 0 | 0 | 0 |
| ARG B 86 | 0 | −15.530 | 0 | 0 | −21.171 | 0 | 0 | 0 | 0 | −9.976 | 0 | 0 |
| ASN B 87 | 0 | 0 | 0 | 0 | 0 | 0 | 0 | 0 | 0 | 0 | 0 | 0 |
| LYS B 88 | 0 | −15.530 | 0 | 0 | −21.171 | 0 | −19.307 | 0 | 0 | −9.976 | 0 | 0 |
| ASN B 89 | 0 | 0 | 0 | 0 | 0 | 0 | 0 | 0 | 0 | 0 | 0 | 0 |
| ASP B 90 | 0 | 0 | 0 | 0 | 0 | 0 | 0 | 0 | 0 | 0 | 0 | 0 |
| LEU B 91 | 0 | 0 | 0 | 0 | 0 | 0 | −19.307 | 0 | 0 | 0 | 0 | 0 |
| THR B 92 | 0 | 0 | 0 | 0 | 0 | 0 | 0 | 0 | 0 | 0 | 0 | 0 |
| ARG B 93 | −22.098 | 0 | 0 | 0 | −20.171 | 0 | −29.307 | 0 | 0 | 0 | −18.528 | −17 |
| GLU B 94 | −22.098 | −19.530 | −5.808 | −13.593 | −25.171 | 0 | −29.307 | 0 | −9.472 | −13.976 | −23.528 | −16 |
| GLU B 95 | 0 | 0 | 0 | 0 | 0 | 0 | −19.307 | 0 | 0 | 0 | 0 | 0 |
| ILE B 96 | 0 | 0 | 0 | 0 | 0 | 0 | 0 | 0 | 0 | 0 | 0 | 0 |
| VAL B 97 | −23.098 | −19.530 | 0 | −13.593 | −25.171 | 0 | −30.307 | 0 | −16.472 | −13.976 | −19.528 | −16 |
| GLU B 98 | −23.098 | −19.530 | 0 | −15.593 | −25.171 | 0 | −30.307 | 0 | −16.472 | 0 | −19.528 | 0 |
| LEU B 99 | 0 | −13.530 | 0 | 0 | −20.171 | 0 | 0 | 0 | 0 | −9.976 | 0 | 0 |
| MET B 100 | 0 | 0 | 0 | 0 | 0 | 0 | 0 | 0 | 0 | 0 | 0 | 0 |
| ARG B 101 | −22.098 | 0 | 0 | −15.593 | 0 | 0 | −30.307 | 0 | −16.472 | 0 | −19.528 | 0 |
| ASP B 102 | −22.098 | 0 | 0 | −15.593 | 0 | 0 | 0 | 0 | 0 | 0 | −18.528 | 0 |

TABLE 1-continued

Fragment Binding Affinity for Caspase-3

| | acet-amide | acetone | benzene | carboxy-lic acid | dimethyl sulfoxide | ethanol | imida-zole | iso-butane | pyrimi-dine | tetra-hydro-furan | urea | H₂O |
|---|---|---|---|---|---|---|---|---|---|---|---|---|
| VAL B 103 | 0 | 0 | 0 | 0 | 0 | 0 | 0 | 0 | 0 | 0 | 0 | 0 |
| SER B 104 | 0 | 0 | 0 | 0 | 0 | 0 | 0 | 0 | 0 | 0 | 0 | 0 |
| LYS B 105 | −22.098 | 0 | 0 | −15.593 | 0 | 0 | 0 | 0 | 0 | 0 | −18.528 | 0 |
| GLU B 106 | 0 | 0 | 0 | 0 | 0 | 0 | 0 | 0 | 0 | 0 | 0 | 0 |
| ASP B 107 | 0 | 0 | 0 | 0 | 0 | 0 | −21.307 | 0 | 0 | 0 | 0 | 0 |
| HIE B 108 | 0 | 0 | 0 | 0 | 0 | 0 | 0 | 0 | 0 | 0 | 0 | 0 |
| SER B 109 | 0 | 0 | 0 | 0 | 0 | 0 | 0 | 0 | 0 | 0 | 0 | 0 |
| LYS B 110 | 0 | 0 | 0 | 0 | 0 | 0 | −22.307 | 0 | 0 | 0 | 0 | 0 |
| ARG B 111 | 0 | 0 | 0 | 0 | 0 | 0 | −21.307 | 0 | 0 | 0 | 0 | −17 |
| SER B 112 | 0 | 0 | 0 | 0 | 0 | 0 | 0 | 0 | 0 | 0 | 0 | 0 |
| SER B 113 | 0 | 0 | 0 | 0 | 0 | 0 | 0 | 0 | 0 | 0 | 0 | 0 |
| PHE B 114 | 0 | 0 | 0 | 0 | 0 | 0 | 0 | 0 | 0 | 0 | 0 | 0 |
| VAL B 115 | 0 | 0 | 0 | 0 | 0 | 0 | 0 | 0 | 0 | 0 | 0 | 0 |
| CYS B 116 | 0 | 0 | 0 | 0 | 0 | 0 | 0 | 0 | 0 | 0 | 0 | 0 |
| VAL B 117 | 0 | 0 | 0 | 0 | 0 | 0 | 0 | 0 | 0 | 0 | 0 | 0 |
| LEU B 118 | 0 | 0 | 0 | 0 | 0 | 0 | 0 | 0 | 0 | 0 | 0 | 0 |
| LEU B 119 | 0 | 0 | 0 | 0 | 0 | 0 | 0 | 0 | 0 | 0 | 0 | 0 |
| SER B 120 | −26.098 | −16.530 | 0 | −21.593 | −27.171 | −26.233 | −35.307 | −4.330 | −29.472 | −19.976 | −30.528 | −21 |
| HIP B 121 | −31.098 | −25.530 | 0 | −27.593 | −29.171 | −26.233 | −35.307 | −6.330 | −29.472 | −19.976 | −35.528 | −23 |
| GLY B 122 | −31.098 | −25.530 | 0 | −17.593 | −29.171 | −22.233 | −31.307 | −4.330 | −16.472 | −19.976 | −35.528 | −21 |
| GLU B 123 | 0 | −25.530 | 0 | 0 | −29.171 | 0 | 0 | 0 | 0 | 0 | 0 | 0 |
| GLU B 124 | 0 | 0 | 0 | 0 | 0 | 0 | 0 | 0 | −13.472 | 0 | 0 | 0 |
| GLY B 125 | 0 | 0 | 0 | 0 | 0 | 0 | 0 | 0 | 0 | 0 | 0 | 0 |
| ILE B 126 | 0 | 0 | 0 | 0 | 0 | 0 | 0 | 0 | 0 | 0 | 0 | 0 |
| ILE B 127 | 0 | 0 | 0 | 0 | 0 | 0 | 0 | 0 | 0 | 0 | 0 | 0 |
| PHE B 128 | 0 | −16.530 | 0 | 0 | 0 | 0 | 0 | 0 | 0 | 0 | 0 | 0 |
| GLY B 129 | 0 | 0 | 0 | 0 | 0 | 0 | 0 | 0 | 0 | 0 | 0 | 0 |
| THR B 130 | 0 | 0 | 0 | 0 | 0 | 0 | 0 | 0 | 0 | 0 | 0 | 0 |
| ASN B 131 | 0 | 0 | 0 | 0 | 0 | 0 | 0 | 0 | 0 | 0 | 0 | 0 |
| GLY B 132 | 0 | 0 | 0 | 0 | 0 | 0 | 0 | 0 | 0 | 0 | 0 | 0 |
| PRO B 133 | 0 | 0 | 0 | 0 | 0 | 0 | 0 | 0 | 0 | 0 | 0 | 0 |
| VAL B 134 | 0 | 0 | 0 | 0 | 0 | 0 | 0 | 0 | 0 | 0 | 0 | 0 |
| ASP B 135 | 0 | 0 | 0 | 0 | −20.171 | 0 | 0 | 0 | 0 | 0 | 0 | 0 |
| LEU B 136 | 0 | 0 | 0 | 0 | 0 | 0 | 0 | 0 | 0 | 0 | 0 | 0 |
| LYS B 137 | −18.098 | 0 | 0 | 0 | 0 | 0 | −24.307 | 0 | −9.472 | 0 | −20.528 | 0 |
| LYS B 138 | −24.098 | −19.530 | −5.808 | 0 | −25.171 | 0 | −30.307 | 0 | −16.472 | −13.976 | −23.528 | −16 |
| ILE B 139 | 0 | 0 | 0 | 0 | 0 | 0 | 0 | 0 | 0 | 0 | 0 | 0 |
| THR B 140 | 0 | 0 | 0 | 0 | 0 | 0 | 0 | 0 | 0 | 0 | 0 | 0 |
| ASN B 141 | −18.098 | 0 | 0 | 0 | 0 | 0 | −24.307 | 0 | −10.472 | 0 | −20.528 | 0 |
| PHE B 142 | 0 | 0 | 0 | 0 | 0 | 0 | 0 | 0 | 0 | 0 | 0 | 0 |
| PHE B 143 | 0 | 0 | 0 | 0 | 0 | 0 | 0 | 0 | 0 | 0 | 0 | 0 |
| ARG B 144 | −26.098 | −16.530 | 0 | 0 | −25.171 | 0 | −30.307 | 0 | −10.472 | −10.976 | −25.528 | 0 |
| GLY B 145 | 0 | 0 | 0 | 0 | 0 | 0 | 0 | 0 | 0 | 0 | 0 | 0 |
| ASP B 146 | 0 | 0 | 0 | 0 | 0 | 0 | 0 | 0 | 0 | 0 | 0 | 0 |
| ARG B 147 | 0 | 0 | 0 | 0 | 0 | 0 | 0 | 0 | 0 | 0 | 0 | 0 |
| CYS B 148 | 0 | 0 | 0 | 0 | 0 | 0 | 0 | 0 | 0 | 0 | 0 | 0 |
| ARG B 149 | 0 | 0 | 0 | 0 | 0 | 0 | 0 | 0 | 0 | 0 | 0 | 0 |
| SER B 150 | 0 | 0 | 0 | 0 | 0 | 0 | 0 | 0 | 0 | 0 | 0 | 0 |
| LEU B 151 | 0 | 0 | 0 | 0 | 0 | 0 | 0 | 0 | 0 | 0 | 0 | 0 |
| THR B 152 | 0 | 0 | 0 | 0 | 0 | 0 | 0 | 0 | 0 | 0 | 0 | −20 |
| GLY B 153 | −23.098 | −15.530 | −7.808 | 0 | −20.171 | 0 | −27.307 | −4.330 | −11.472 | −15.976 | 0 | −20 |
| LYS B 154 | 0 | 0 | 0 | 0 | 0 | 0 | 0 | 0 | 0 | 0 | 0 | 0 |
| PRO B 155 | 0 | 0 | 0 | 0 | 0 | 0 | 0 | 0 | 0 | 0 | 0 | 0 |
| LYS B 156 | 0 | 0 | 0 | 0 | 0 | 0 | 0 | 0 | 0 | 0 | 0 | −20 |
| LEU B 157 | 0 | 0 | 0 | 0 | 0 | 0 | 0 | 0 | 0 | 0 | 0 | 0 |
| PHE B 158 | 0 | 0 | 0 | 0 | 0 | 0 | 0 | 0 | 0 | 0 | 0 | 0 |
| ILE B 159 | 0 | 0 | 0 | 0 | 0 | 0 | 0 | 0 | 0 | 0 | 0 | 0 |
| ILE B 160 | 0 | 0 | 0 | 0 | 0 | 0 | 0 | 0 | 0 | 0 | 0 | 0 |
| GLN B 161 | −27.098 | −16.530 | 0 | 0 | −29.171 | −18.233 | −19.307 | −4.330 | −17.472 | −19.976 | −26.528 | 0 |
| ALA B 162 | −31.098 | −25.530 | 0 | −21.593 | −29.171 | −26.233 | −35.307 | −4.330 | −17.472 | −19.976 | −34.528 | −21 |
| CYM B 163 | −31.098 | −25.530 | 0 | −27.593 | −29.171 | −26.233 | −35.307 | −6.330 | −29.472 | −19.976 | −34.528 | −23 |
| ARG B 164 | 0 | 0 | 0 | 0 | 0 | 0 | 0 | 0 | −14.472 | 0 | 0 | 0 |
| GLY B 165 | 0 | 0 | 0 | 0 | 0 | 0 | 0 | 0 | 0 | 0 | 0 | 0 |
| THR B 166 | 0 | 0 | 0 | 0 | 0 | 0 | 0 | 0 | 0 | 0 | 0 | 0 |
| GLU B 167 | −24.098 | −13.530 | 0 | −13.593 | −16.171 | −15.233 | −25.307 | 0 | 0 | −9.976 | −23.528 | −21 |
| LEU B 168 | −24.098 | 0 | −5.808 | 0 | −16.171 | −15.233 | −21.307 | 0 | 0 | −9.976 | 0 | 0 |
| ASP B 169 | 0 | 0 | 0 | 0 | 0 | 0 | 0 | 0 | 0 | 0 | 0 | 0 |
| CYS B 170 | 0 | 0 | 0 | 0 | 0 | 0 | 0 | 0 | 0 | 0 | 0 | 0 |
| GLY B 171 | 0 | 0 | 0 | 0 | 0 | 0 | 0 | 0 | 0 | 0 | 0 | 0 |
| ILE B 172 | 0 | 0 | 0 | 0 | 0 | 0 | 0 | 0 | 0 | 0 | 0 | 0 |
| GLU B 173 | 0 | 0 | 0 | 0 | 0 | 0 | −19.307 | 0 | 0 | 0 | −22.528 | 0 |
| NME B 999 | 0 | 0 | 0 | 0 | 0 | 0 | 0 | 0 | 0 | 0 | 0 | 0 |
| ACE F 0 | 0 | 0 | 0 | 0 | 0 | 0 | 0 | 0 | 0 | 0 | 0 | 0 |

TABLE 1-continued

Fragment Binding Affinity for Caspase-3

| | acet-amide | acetone | benzene | carboxy-lic acid | dimethyl sulfoxide | ethanol | imida-zole | iso-butane | pyrimi-dine | tetra-hydro-furan | urea | $H_2O$ |
|---|---|---|---|---|---|---|---|---|---|---|---|---|
| HID F 185 | 0 | −14.530 | −7.808 | 0 | −20.171 | 0 | −27.307 | −4.330 | −11.472 | −15.976 | 0 | 0 |
| LYS F 186 | 0 | 0 | 0 | −16.593 | 0 | 0 | 0 | 0 | 0 | 0 | 0 | 0 |
| ILE F 187 | −23.098 | −14.530 | 0 | 0 | −20.171 | 0 | −27.307 | −4.330 | −11.472 | −15.976 | 0 | −20 |
| PRO F 188 | 0 | 0 | 0 | 0 | 0 | 0 | 0 | 0 | 0 | 0 | 0 | 0 |
| VAL F 189 | 0 | 0 | 0 | 0 | 0 | 0 | 0 | 0 | 0 | 0 | 0 | 0 |
| ASP F 190 | 0 | 0 | 0 | 0 | 0 | 0 | 0 | 0 | 0 | 0 | 0 | 0 |
| ALA F 191 | 0 | 0 | 0 | 0 | 0 | 0 | 0 | 0 | 0 | 0 | 0 | −20 |
| ASP F 192 | −23.098 | −14.530 | 0 | 0 | −20.171 | 0 | −27.307 | 0 | −11.472 | −15.976 | 0 | −20 |
| PHE F 193 | 0 | 0 | 0 | 0 | 0 | 0 | 0 | 0 | 0 | 0 | 0 | 0 |
| LEU F 194 | 0 | 0 | 0 | 0 | 0 | 0 | 0 | 0 | 0 | 0 | 0 | 0 |
| TYR F 195 | 0 | 0 | 0 | 0 | 0 | 0 | 0 | 0 | 0 | 0 | 0 | 0 |
| ALA F 196 | 0 | 0 | 0 | 0 | 0 | 0 | 0 | 0 | 0 | 0 | 0 | 0 |
| TYR F 197 | 0 | 0 | 0 | 0 | 0 | 0 | 0 | 0 | 0 | 0 | 0 | 0 |
| SER F 198 | 0 | 0 | 0 | 0 | 0 | 0 | 0 | 0 | 0 | 0 | 0 | 0 |
| THR F 199 | 0 | 0 | 0 | 0 | 0 | 0 | 0 | 0 | 0 | 0 | 0 | 0 |
| ALA F 200 | 0 | 0 | 0 | 0 | 0 | 0 | 0 | 0 | 0 | 0 | 0 | 0 |
| PRO F 201 | 0 | 0 | −7.808 | −13.593 | 0 | −11.233 | 0 | −4.330 | −12.472 | 0 | 0 | −21 |
| GLY F 202 | 0 | 0 | 0 | −13.593 | 0 | 0 | 0 | 0 | 0 | 0 | 0 | 0 |
| TYR F 203 | −24.098 | 0 | −7.808 | 0 | 0 | −15.233 | 0 | 0 | 0 | 0 | −18.528 | −21 |
| TYR F 204 | 0 | 0 | 0 | 0 | −29.171 | −11.233 | 0 | −4.330 | −17.472 | −15.976 | 0 | 0 |
| SER F 205 | −31.098 | −25.530 | 0 | −21.593 | −29.171 | −26.233 | −35.307 | −4.330 | −29.472 | −19.976 | −34.528 | −21 |
| TRP F 206 | 0 | 0 | 0 | 0 | 0 | 0 | 0 | −4.330 | −17.472 | 0 | 0 | 0 |
| ARG F 207 | −31.098 | −25.530 | −5.808 | −21.593 | −29.171 | −26.233 | −35.307 | −4.330 | −29.472 | −19.976 | −34.528 | 0 |
| ASN F 208 | 0 | 0 | 0 | 0 | 0 | 0 | 0 | 0 | −10.472 | 0 | 0 | 0 |
| SER F 209 | 0 | 0 | 0 | 0 | 0 | 0 | 0 | 0 | 0 | 0 | 0 | 0 |
| LYS F 210 | 0 | 0 | 0 | 0 | 0 | 0 | 0 | 0 | 0 | 0 | 0 | 0 |
| ASP F 211 | 0 | 0 | 0 | 0 | 0 | 0 | 0 | 0 | 0 | 0 | 0 | 0 |
| GLY F 212 | 0 | 0 | 0 | 0 | 0 | 0 | 0 | 0 | 0 | 0 | 0 | 0 |
| SER F 213 | 0 | 0 | 0 | 0 | 0 | 0 | 0 | 0 | 0 | 0 | 0 | 0 |
| TRP F 214 | 0 | 0 | 0 | 0 | 0 | 0 | 0 | 0 | −10.472 | 0 | 0 | 0 |
| PHE F 215 | 0 | 0 | 0 | 0 | 0 | 0 | 0 | 0 | 0 | 0 | 0 | 0 |
| ILE F 216 | 0 | 0 | 0 | 0 | 0 | 0 | 0 | 0 | 0 | 0 | 0 | 0 |
| GLN F 217 | 0 | 0 | 0 | 0 | 0 | 0 | 0 | 0 | 0 | 0 | 0 | 0 |
| SER F 218 | 0 | 0 | 0 | 0 | 0 | 0 | 0 | 0 | 0 | 0 | 0 | 0 |
| LEU F 219 | 0 | 0 | 0 | 0 | 0 | 0 | 0 | 0 | 0 | 0 | 0 | 0 |
| CYS F 220 | 0 | 0 | 0 | 0 | 0 | 0 | 0 | 0 | 0 | 0 | 0 | 0 |
| ALA F 221 | 0 | 0 | 0 | 0 | 0 | 0 | 0 | 0 | 0 | 0 | 0 | 0 |
| MET F 222 | 0 | 0 | −6.808 | 0 | 0 | 0 | 0 | 0 | −13.472 | −13.976 | 0 | 0 |
| LEU F 223 | 0 | 0 | 0 | 0 | 0 | 0 | 0 | 0 | 0 | 0 | 0 | 0 |
| LYS F 224 | 0 | 0 | 0 | 0 | 0 | 0 | 0 | 0 | 0 | 0 | 0 | 0 |
| GLN F 225 | 0 | 0 | 0 | 0 | −16.171 | 0 | 0 | 0 | 0 | 0 | 0 | 0 |
| TYR F 226 | 0 | 0 | 0 | 0 | 0 | 0 | 0 | 0 | 0 | 0 | 0 | 0 |
| ALA F 227 | 0 | 0 | 0 | 0 | 0 | 0 | 0 | 0 | 0 | 0 | 0 | 0 |
| ASP F 228 | 0 | 0 | 0 | 0 | −16.171 | 0 | 0 | 0 | 0 | 0 | −17.528 | 0 |
| LYS F 229 | 0 | 0 | 0 | 0 | −16.171 | 0 | 0 | 0 | 0 | 0 | −17.528 | 0 |
| LEU F 230 | −25.098 | −18.530 | 0 | −19.593 | −19.171 | 0 | 0 | 0 | −12.472 | 0 | −22.528 | 0 |
| GLU F 231 | 0 | 0 | 0 | 0 | 0 | 0 | 0 | 0 | 0 | 0 | 0 | 0 |
| PHE F 232 | 0 | 0 | 0 | 0 | 0 | 0 | 0 | 0 | 0 | 0 | 0 | 0 |
| MET F 233 | 0 | 0 | 0 | 0 | 0 | 0 | 0 | 0 | 0 | 0 | 0 | 0 |
| HIE F 234 | 0 | 0 | 0 | 0 | 0 | 0 | 0 | 0 | 0 | 0 | 0 | 0 |
| ILE F 235 | 0 | 0 | 0 | 0 | 0 | 0 | 0 | 0 | 0 | 0 | 0 | 0 |
| LEU F 236 | 0 | 0 | 0 | 0 | 0 | 0 | 0 | 0 | 0 | 0 | 0 | 0 |
| THR F 237 | 0 | 0 | 0 | 0 | 0 | 0 | 0 | 0 | 0 | 0 | 0 | 0 |
| ARG F 238 | −25.098 | −18.530 | 0 | −19.593 | −23.171 | −22.233 | −27.307 | 0 | −13.472 | −12.976 | −22.528 | −21 |
| VAL F 239 | 0 | 0 | 0 | 0 | 0 | 0 | 0 | 0 | 0 | 0 | 0 | 0 |
| ASN F 240 | 0 | 0 | 0 | 0 | 0 | 0 | 0 | 0 | 0 | 0 | 0 | 0 |
| ARG F 241 | −24.098 | −15.530 | −8.808 | 0 | −20.171 | 0 | −26.307 | 0 | −13.472 | −13.976 | −23.528 | 0 |
| LYS F 242 | −24.098 | −13.530 | −5.808 | 0 | 0 | 0 | −26.307 | 0 | −13.472 | −13.976 | −20.528 | 0 |
| VAL F 243 | 0 | 0 | 0 | 0 | 0 | 0 | 0 | 0 | 0 | 0 | 0 | 0 |
| ALA F 244 | 0 | 0 | 0 | 0 | 0 | 0 | 0 | 0 | 0 | 0 | 0 | 0 |
| THR F 245 | −24.098 | −15.530 | −6.808 | −19.593 | −18.171 | 0 | −19.307 | 0 | −13.472 | −9.976 | −23.528 | 0 |
| GLU F 246 | −24.098 | −15.530 | 0 | 0 | −20.171 | 0 | −26.307 | 0 | −13.472 | −13.976 | −23.528 | 0 |
| PHE F 247 | 0 | −15.530 | 0 | 0 | 0 | 0 | 0 | 0 | 0 | 0 | 0 | 0 |
| GLU F 248 | 0 | −15.530 | 0 | −19.593 | −18.171 | −12.233 | 0 | 0 | −10.472 | 0 | −18.528 | −16 |
| SER F 249 | 0 | 0 | 0 | 0 | 0 | 0 | 0 | 0 | −10.472 | 0 | 0 | 0 |
| PHE F 250 | 0 | 0 | 0 | 0 | 0 | 0 | 0 | 0 | −10.472 | 0 | 0 | 0 |
| SER F 251 | 0 | 0 | 0 | 0 | 0 | 0 | 0 | 0 | 0 | 0 | 0 | 0 |
| PHE F 252 | 0 | 0 | 0 | 0 | 0 | 0 | 0 | 0 | 0 | 0 | 0 | 0 |
| ASP F 253 | 0 | 0 | 0 | 0 | 0 | 0 | 0 | 0 | 0 | 0 | 0 | 0 |
| ALA F 254 | 0 | 0 | 0 | 0 | 0 | 0 | 0 | 0 | 0 | 0 | 0 | 0 |
| THR F 255 | 0 | 0 | 0 | 0 | 0 | 0 | 0 | 0 | 0 | 0 | 0 | 0 |
| PHE F 256 | 0 | 0 | 0 | 0 | 0 | 0 | 0 | 0 | 0 | 0 | 0 | 0 |
| HIE F 257 | 0 | 0 | 0 | 0 | 0 | 0 | 0 | 0 | 0 | 0 | 0 | 0 |

TABLE 1-continued

Fragment Binding Affinity for Caspase-3

| | acet-amide | acetone | benzene | carboxylic acid | dimethyl sulfoxide | ethanol | imidazole | iso-butane | pyrimidine | tetra-hydrofuran | urea | H$_2$O |
|---|---|---|---|---|---|---|---|---|---|---|---|---|
| ALA F 258 | 0 | 0 | 0 | −12.593 | 0 | −12.233 | 0 | 0 | 0 | 0 | 0 | 0 |
| LYS F 259 | 0 | 0 | 0 | 0 | 0 | 0 | 0 | 0 | 0 | 0 | 0 | 0 |
| LYS F 260 | 0 | −15.530 | 0 | −19.593 | −18.171 | 0 | 0 | 0 | 0 | 0 | −18.528 | −16 |
| GLN F 261 | 0 | 0 | 0 | 0 | 0 | 0 | 0 | 0 | 0 | 0 | 0 | 0 |
| ILE F 262 | 0 | 0 | 0 | 0 | 0 | 0 | 0 | 0 | 0 | 0 | 0 | 0 |
| PRO F 263 | 0 | 0 | 0 | 0 | 0 | 0 | 0 | 0 | 0 | 0 | 0 | 0 |
| CYS F 264 | 0 | 0 | 0 | 0 | 0 | 0 | 0 | 0 | 0 | 0 | 0 | 0 |
| ILE F 265 | 0 | 0 | 0 | 0 | 0 | 0 | 0 | 0 | 0 | 0 | 0 | 0 |
| VAL F 266 | 0 | 0 | 0 | 0 | 0 | 0 | 0 | 0 | 0 | 0 | 0 | 0 |
| SER F 267 | 0 | 0 | 0 | 0 | 0 | 0 | 0 | 0 | 0 | 0 | 0 | 0 |
| MET F 268 | 0 | 0 | 0 | 0 | 0 | 0 | 0 | 0 | 0 | 0 | 0 | 0 |
| LEU F 269 | 0 | 0 | 0 | 0 | 0 | 0 | 0 | 0 | 0 | 0 | 0 | 0 |
| THR F 270 | −23.098 | −14.530 | 0 | 0 | −20.171 | 0 | −27.307 | −4.330 | −11.472 | −15.976 | 0 | 0 |
| LYS F 271 | −23.098 | −15.530 | −7.808 | 0 | −20.171 | 0 | −27.307 | −4.330 | −11.472 | −15.976 | 0 | 0 |
| GLU F 272 | −18.098 | −13.530 | 0 | −16.593 | −17.171 | −15.233 | −21.307 | 0 | 0 | 0 | −20.528 | −26 |
| LEU F 273 | 0 | 0 | 0 | 0 | 0 | 0 | 0 | 0 | 0 | 0 | 0 | 0 |
| TYR F 274 | 0 | −13.530 | 0 | 0 | 0 | 0 | 0 | 0 | 0 | 0 | 0 | 0 |
| PHE F 275 | 0 | 0 | 0 | 0 | 0 | 0 | 0 | 0 | 0 | 0 | 0 | 0 |
| TYR F 276 | 0 | 0 | 0 | 0 | 0 | 0 | 0 | 0 | 0 | 0 | 0 | 0 |
| HID F 277 | 0 | 0 | 0 | 0 | 0 | 0 | 0 | 0 | 0 | 0 | 0 | 0 |
| NME F 999 | 0 | 0 | 0 | 0 | 0 | 0 | 0 | 0 | 0 | 0 | 0 | 0 |

Example 2

The following data in Table 2 was generated from a simulation conducted according to the methods of the present invention on the protein Caspase-8. Amino acid residue are listed on the left hand side, while different fragment types are listed at the top. The binding affinities B$_c$ associated with the fragment-residue pairs are listed.

TABLE 2

Fragment Binding Affinity for Caspase-8

| | acet-amide | acetone | benzene | carboxylic acid | dimethyl sulfoxide | ethanol | imidazole | iso-butane | pyrimidine | tetra-hydrofuran | urea | H$_2$O |
|---|---|---|---|---|---|---|---|---|---|---|---|---|
| ACE A 0 | −27.098 | −8.530 | 0 | 0 | −11.171 | 0 | −14.307 | 0 | 0 | −6.976 | −22.528 | −17 |
| ASP A 223 | −27.098 | −20.530 | −3.808 | −12.593 | −22.171 | −13.233 | −30.307 | 0 | −14.472 | −11.976 | −22.528 | −17 |
| LYS A 224 | −27.098 | −20.530 | −3.808 | −12.593 | −22.171 | −14.233 | −30.307 | 0 | −14.472 | −11.976 | −22.528 | −16 |
| VAL A 225 | −13.098 | −11.530 | −4.808 | −12.593 | −15.171 | −10.233 | 0 | −2.330 | −9.472 | −9.976 | −19.528 | 0 |
| TYR A 226 | −26.098 | −21.530 | −4.808 | −10.593 | −26.171 | −16.233 | −20.307 | −2.330 | −11.472 | −11.976 | −20.528 | −11 |
| GLN A 227 | −26.098 | −21.530 | −4.808 | −10.593 | −26.171 | −11.233 | −20.307 | −2.330 | −11.472 | −11.976 | −20.528 | −11 |
| MET A 228 | −13.098 | −12.530 | 0 | −10.593 | −18.171 | 0 | −13.307 | 0 | −9.472 | −8.976 | −22.528 | 0 |
| LYS A 229 | −22.098 | −12.530 | −4.808 | −13.593 | −18.171 | −15.233 | −25.307 | −2.330 | −11.472 | −7.976 | −30.528 | 0 |
| SER A 230 | 0 | 0 | 0 | 0 | 0 | 0 | 0 | 0 | 0 | 0 | 0 | 0 |
| LYS A 231 | 0 | 0 | 0 | −13.593 | 0 | −15.233 | 0 | 0 | −7.472 | 0 | 0 | −12 |
| PRO A 232 | 0 | 0 | 0 | 0 | 0 | 0 | 0 | 0 | 0 | 0 | 0 | 0 |
| ARG A 233 | 0 | 0 | 0 | −13.593 | 0 | −15.233 | 0 | 0 | 0 | 0 | 0 | −12 |
| GLY A 234 | 0 | 0 | 0 | 0 | 0 | 0 | 0 | 0 | 0 | 0 | 0 | 0 |
| TYR A 235 | 0 | 0 | 0 | −8.593 | 0 | 0 | 0 | 0 | 0 | 0 | 0 | 0 |
| CYS A 236 | 0 | 0 | 0 | 0 | 0 | 0 | 0 | 0 | 0 | 0 | 0 | 0 |
| LEU A 237 | 0 | 0 | 0 | 0 | 0 | 0 | 0 | 0 | 0 | 0 | 0 | 0 |
| ILE A 238 | 0 | 0 | 0 | 0 | 0 | 0 | 0 | 0 | 0 | 0 | 0 | 0 |
| ILE A 239 | 0 | 0 | 0 | 0 | 0 | 0 | 0 | 0 | 0 | 0 | 0 | 0 |
| ASN A 240 | 0 | 0 | 0 | 0 | 0 | 0 | 0 | 0 | 0 | 0 | 0 | 0 |
| ASN A 241 | 0 | 0 | 0 | 0 | 0 | 0 | 0 | 0 | 0 | 0 | 0 | 0 |
| HID A 242 | 0 | −11.530 | 0 | 0 | 0 | 0 | −14.307 | 0 | 0 | 0 | 0 | 0 |
| ASN A 243 | 0 | 0 | 0 | 0 | 0 | −9.233 | 0 | 0 | 0 | 0 | 0 | 0 |
| PHE A 244 | 0 | 0 | 0 | 0 | 0 | 0 | 0 | 0 | 0 | 0 | 0 | 0 |
| ALA A 245 | 0 | 0 | −3.808 | 0 | 0 | 0 | 0 | 0 | 0 | 0 | 0 | 0 |
| LYS A 246 | −15.098 | −11.530 | −4.808 | −8.593 | −15.171 | −9.233 | −17.307 | 0 | −15.472 | −6.976 | −12.528 | −11 |
| ALA A 247 | 0 | 0 | 0 | 0 | 0 | 0 | 0 | 0 | 0 | 0 | 0 | 0 |
| ARG A 248 | 0 | 0 | 0 | 0 | 0 | 0 | 0 | 0 | 0 | 0 | 0 | 0 |
| GLU A 249 | 0 | 0 | 0 | 0 | 0 | 0 | 0 | 0 | 0 | 0 | 0 | 0 |
| LYS A 250 | −28.098 | −12.530 | −3.808 | −15.593 | −11.171 | −13.233 | −23.307 | 0 | −15.472 | −8.976 | −32.528 | −14 |
| VAL A 251 | 0 | 0 | 0 | 0 | 0 | 0 | 0 | 0 | 0 | 0 | 0 | −11 |
| PRO A 252 | 0 | 0 | 0 | 0 | 0 | 0 | 0 | 0 | 0 | 0 | 0 | 0 |
| LYS A 253 | −14.098 | −8.530 | 0 | −11.593 | −10.171 | −12.233 | −14.307 | −2.330 | −9.472 | 0 | −17.528 | −14 |
| LEU A 254 | 0 | 0 | 0 | 0 | 0 | 0 | 0 | −2.330 | 0 | 0 | 0 | 0 |
| HID A 255 | 0 | 0 | 0 | 0 | 0 | 0 | 0 | 0 | 0 | 0 | 0 | 0 |

TABLE 2-continued

Fragment Binding Affinity for Caspase-8

| | acet-amide | acetone | benzene | carboxy-lic acid | dimethyl sulfoxide | ethanol | imidazole | iso-butane | pyrimi-dine | tetra-hydro-furan | urea | H$_2$O |
|---|---|---|---|---|---|---|---|---|---|---|---|---|
| SER A 256 | 0 | 0 | 0 | 0 | 0 | 0 | 0 | 0 | 0 | 0 | 0 | 0 |
| ILE A 257 | 0 | 0 | −3.808 | 0 | 0 | 0 | 0 | −3.330 | 0 | 0 | 0 | 0 |
| ARG A 258 | 0 | 0 | −8.808 | −7.593 | 0 | −12.233 | −15.307 | −2.330 | −11.472 | −6.976 | 0 | 0 |
| ASP A 259 | −14.098 | 0 | −8.808 | −7.593 | 0 | −12.233 | −15.307 | 0 | −11.472 | 0 | −12.528 | 0 |
| ARG A 260 | −30.098 | −25.530 | −8.808 | −22.593 | −28.171 | −18.233 | −32.307 | 0 | 0 | −16.976 | −31.528 | −10 |
| ASN A 261 | −14.098 | −11.530 | 0 | −7.593 | 0 | −12.233 | −15.307 | 0 | −11.472 | 0 | −12.528 | 0 |
| GLY A 262 | 0 | −11.530 | 0 | 0 | 0 | 0 | 0 | 0 | 0 | 0 | 0 | 0 |
| THR A 263 | 0 | −11.530 | 0 | 0 | 0 | 0 | 0 | 0 | 0 | 0 | 0 | 0 |
| HIE A 264 | 0 | −11.530 | 0 | 0 | 0 | 0 | −14.307 | 0 | 0 | 0 | 0 | 0 |
| LEU A 265 | 0 | 0 | 0 | 0 | 0 | 0 | 0 | 0 | 0 | 0 | 0 | 0 |
| ASP A 266 | 0 | 0 | 0 | 0 | 0 | 0 | 0 | 0 | 0 | 0 | 0 | 0 |
| ALA A 267 | 0 | 0 | 0 | 0 | 0 | 0 | 0 | 0 | 0 | 0 | 0 | 0 |
| GLY A 268 | 0 | 0 | 0 | 0 | 0 | 0 | 0 | 0 | 0 | 0 | 0 | 0 |
| ALA A 269 | 0 | 0 | 0 | 0 | 0 | 0 | 0 | −2.330 | 0 | 0 | 0 | 0 |
| LEU A 270 | 0 | 0 | 0 | 0 | 0 | 0 | 0 | 0 | 0 | 0 | 0 | 0 |
| THR A 271 | 0 | 0 | 0 | 0 | 0 | 0 | 0 | 0 | 0 | 0 | 0 | 0 |
| THR A 272 | 0 | 0 | 0 | 0 | 0 | 0 | 0 | 0 | 0 | 0 | 0 | 0 |
| THR A 273 | 0 | 0 | 0 | 0 | 0 | 0 | 0 | 0 | 0 | 0 | 0 | 0 |
| PHE A 274 | 0 | 0 | 0 | 0 | 0 | 0 | 0 | 0 | 0 | 0 | 0 | 0 |
| GLU A 275 | 0 | 0 | 0 | 0 | 0 | 0 | 0 | 0 | 0 | 0 | 0 | 0 |
| GLU A 276 | 0 | 0 | 0 | 0 | 0 | 0 | 0 | 0 | 0 | 0 | 0 | 0 |
| LEU A 277 | 0 | 0 | 0 | 0 | 0 | 0 | 0 | 0 | 0 | 0 | 0 | 0 |
| HIE A 278 | 0 | 0 | 0 | 0 | 0 | 0 | 0 | 0 | 0 | 0 | 0 | 0 |
| PHE A 279 | 0 | 0 | 0 | 0 | 0 | 0 | 0 | 0 | 0 | 0 | 0 | 0 |
| GLU A 280 | 0 | 0 | 0 | −9.593 | 0 | 0 | 0 | 0 | 0 | 0 | 0 | 0 |
| ILE A 281 | 0 | 0 | 0 | 0 | 0 | 0 | 0 | 0 | 0 | 0 | 0 | 0 |
| LYS A 282 | 0 | 0 | 0 | −9.593 | 0 | 0 | 0 | 0 | 0 | 0 | 0 | 0 |
| PRO A 283 | 0 | 0 | 0 | 0 | 0 | 0 | 0 | 0 | 0 | 0 | 0 | 0 |
| HID A 284 | 0 | 0 | 0 | 0 | 0 | 0 | 0 | 0 | 0 | 0 | 0 | 0 |
| ASP A 285 | 0 | 0 | 0 | 0 | 0 | 0 | −14.307 | −2.330 | 0 | 0 | 0 | 0 |
| ASP A 286 | −13.098 | −11.530 | −3.808 | −8.593 | −14.171 | −9.233 | −16.307 | 0 | −7.472 | 0 | −12.528 | −10 |
| CYS A 287 | 0 | 0 | 0 | 0 | 0 | 0 | 0 | 0 | 0 | 0 | 0 | 0 |
| THR A 288 | −15.098 | −11.530 | 0 | −15.593 | −12.171 | 0 | −13.307 | 0 | −15.472 | 0 | 0 | 0 |
| VAL A 289 | 0 | 0 | 0 | 0 | 0 | 0 | 0 | 0 | 0 | 0 | 0 | 0 |
| GLU A 290 | −28.098 | −12.530 | 0 | −15.593 | −11.171 | −13.233 | −23.307 | 0 | 0 | 0 | −32.528 | −10 |
| GLN A 291 | −15.098 | −11.530 | 0 | −8.593 | −14.171 | −9.233 | −18.307 | 0 | 0 | −6.976 | −12.528 | 0 |
| ILE A 292 | 0 | 0 | 0 | 0 | 0 | 0 | 0 | 0 | 0 | 0 | 0 | 0 |
| TYR A 293 | 0 | 0 | 0 | 0 | 0 | 0 | 0 | 0 | 0 | 0 | 0 | 0 |
| GLU A 294 | −15.098 | −9.530 | 0 | 0 | −13.171 | 0 | −21.307 | 0 | 0 | −6.976 | −15.528 | 0 |
| ILE A 295 | 0 | 0 | 0 | 0 | 0 | 0 | 0 | 0 | 0 | 0 | 0 | 0 |
| LEU A 296 | 0 | 0 | 0 | 0 | 0 | 0 | 0 | 0 | 0 | 0 | 0 | 0 |
| LYS A 297 | −15.098 | −9.530 | −3.808 | 0 | −13.171 | 0 | −21.307 | 0 | 0 | −6.976 | −15.528 | 0 |
| ILE A 298 | 0 | 0 | 0 | 0 | 0 | 0 | −13.307 | 0 | 0 | −6.976 | −15.528 | 0 |
| TYR A 299 | 0 | 0 | 0 | 0 | 0 | 0 | 0 | 0 | 0 | 0 | 0 | 0 |
| GLN A 300 | −13.098 | −11.530 | 0 | −11.593 | −12.171 | 0 | −13.307 | 0 | −8.472 | −8.976 | 0 | 0 |
| LEU A 301 | −13.098 | −11.530 | 0 | −11.593 | −12.171 | 0 | −13.307 | 0 | −8.472 | −8.976 | 0 | 0 |
| MET A 302 | −13.098 | −11.530 | 0 | −11.593 | −12.171 | 0 | −13.307 | 0 | −8.472 | −6.976 | 0 | 0 |
| ASP A 303 | −13.098 | −11.530 | 0 | 0 | −12.171 | 0 | 0 | 0 | 0 | 0 | 0 | 0 |
| HIE A 304 | 0 | 0 | 0 | 0 | 0 | 0 | 0 | 0 | 0 | 0 | 0 | 0 |
| SER A 305 | 0 | 0 | 0 | 0 | 0 | 0 | 0 | 0 | 0 | 0 | 0 | 0 |
| ASN A 306 | 0 | 0 | 0 | 0 | 0 | 0 | 0 | 0 | 0 | 0 | 0 | 0 |
| MET A 307 | 0 | 0 | 0 | 0 | 0 | 0 | 0 | 0 | 0 | 0 | 0 | 0 |
| ASP A 308 | 0 | 0 | 0 | 0 | 0 | 0 | −20.307 | 0 | −7.472 | 0 | −17.528 | −11 |
| CYS A 309 | 0 | 0 | 0 | 0 | 0 | 0 | 0 | 0 | 0 | 0 | 0 | 0 |
| PHE A 310 | 0 | 0 | 0 | 0 | 0 | 0 | 0 | 0 | 0 | 0 | 0 | 0 |
| ILE A 311 | 0 | 0 | 0 | 0 | 0 | 0 | 0 | 0 | 0 | 0 | 0 | 0 |
| CYS A 312 | 0 | 0 | 0 | 0 | 0 | 0 | 0 | 0 | 0 | 0 | 0 | 0 |
| CYS A 313 | 0 | 0 | 0 | 0 | 0 | 0 | 0 | 0 | 0 | 0 | 0 | 0 |
| ILE A 314 | 0 | 0 | 0 | 0 | 0 | 0 | 0 | 0 | 0 | 0 | 0 | 0 |
| LEU A 315 | 0 | 0 | 0 | 0 | 0 | 0 | 0 | 0 | 0 | 0 | 0 | 0 |
| SER A 316 | −27.098 | −25.530 | −8.808 | 0 | 0 | −18.233 | −25.307 | 0 | 0 | −16.976 | 0 | 0 |
| HIE A 317 | −26.098 | −25.530 | −8.808 | −22.593 | −28.171 | −18.233 | −32.307 | −3.330 | 0 | −16.976 | 0 | 0 |
| GLY A 318 | 0 | 0 | 0 | 0 | 0 | 0 | 0 | −2.330 | 0 | 0 | 0 | 0 |
| ASP A 319 | −14.098 | −10.530 | −3.808 | −11.593 | −15.171 | −11.233 | −20.307 | 0 | −9.472 | −7.976 | −17.528 | −14 |
| LYS A 320 | −23.098 | −15.530 | −3.808 | −8.593 | −18.171 | −9.233 | −26.307 | 0 | −10.472 | −7.976 | −24.528 | 0 |
| GLY A 321 | 0 | 0 | 0 | 0 | 0 | 0 | 0 | −2.330 | 0 | 0 | 0 | 0 |
| ILE A 322 | 0 | 0 | 0 | −12.593 | 0 | 0 | 0 | 0 | 0 | 0 | 0 | 0 |
| ILE A 323 | 0 | 0 | 0 | 0 | 0 | 0 | 0 | 0 | 0 | 0 | 0 | 0 |
| TYR A 324 | 0 | 0 | 0 | 0 | 0 | 0 | 0 | −2.330 | 0 | 0 | 0 | 0 |
| GLY A 325 | 0 | 0 | 0 | 0 | 0 | 0 | 0 | 0 | 0 | 0 | 0 | 0 |
| THR A 326 | 0 | 0 | 0 | 0 | 0 | 0 | 0 | 0 | 0 | 0 | 0 | 0 |
| ASP A 327 | −28.098 | −12.530 | 0 | −15.593 | −11.171 | −13.233 | −23.307 | 0 | −15.472 | −8.976 | −32.528 | −14 |
| GLY A 328 | 0 | 0 | 0 | 0 | 0 | 0 | 0 | 0 | 0 | 0 | 0 | 0 |

TABLE 2-continued

Fragment Binding Affinity for Caspase-8

| | acet-amide | acetone | benzene | carboxy-lic acid | dimethyl sulfoxide | ethanol | imidazole | iso-butane | pyrimi-dine | tetra-hydro-furan | urea | $H_2O$ |
|---|---|---|---|---|---|---|---|---|---|---|---|---|
| GLN A 329 | 0 | 0 | 0 | −7.593 | −10.171 | 0 | 0 | 0 | 0 | 0 | 0 | −11 |
| GLU A 330 | 0 | −8.530 | 0 | −11.593 | −10.171 | −12.233 | −14.307 | 0 | −9.472 | 0 | −17.528 | −11 |
| ALA A 331 | 0 | 0 | 0 | 0 | 0 | 0 | 0 | 0 | 0 | 0 | 0 | 0 |
| PRO A 332 | 0 | 0 | 0 | 0 | 0 | 0 | 0 | 0 | 0 | 0 | 0 | 0 |
| ILE A 333 | 0 | 0 | 0 | 0 | 0 | 0 | 0 | 0 | 0 | 0 | 0 | 0 |
| TYR A 334 | 0 | 0 | 0 | 0 | 0 | 0 | 0 | −2.330 | 0 | 0 | 0 | 0 |
| GLU A 335 | −14.098 | 0 | 0 | 0 | 0 | −7.233 | −17.307 | 0 | 0 | 0 | −16.528 | 0 |
| LEU A 336 | 0 | 0 | 0 | 0 | 0 | 0 | 0 | 0 | 0 | 0 | 0 | 0 |
| THR A 337 | 0 | 0 | 0 | 0 | 0 | 0 | 0 | 0 | 0 | 0 | 0 | 0 |
| SER A 338 | −14.098 | 0 | 0 | 0 | 0 | −7.233 | 0 | 0 | 0 | 0 | 0 | 0 |
| GLN A 339 | −14.098 | 0 | 0 | 0 | 0 | 0 | −17.307 | 0 | 0 | 0 | −16.528 | 0 |
| PHE A 340 | 0 | 0 | 0 | 0 | 0 | 0 | 0 | 0 | 0 | 0 | 0 | 0 |
| THR A 341 | 0 | 0 | 0 | 0 | 0 | −8.233 | 0 | 0 | 0 | 0 | 0 | 0 |
| GLY A 342 | −16.098 | 0 | 0 | 0 | 0 | −7.233 | 0 | −2.330 | 0 | 0 | −13.528 | 0 |
| LEU A 343 | 0 | 0 | 0 | 0 | 0 | 0 | 0 | −2.330 | 0 | 0 | 0 | 0 |
| LYS A 344 | −14.098 | −8.530 | −3.808 | 0 | −11.171 | −8.233 | −17.307 | 0 | 0 | 0 | −16.528 | 0 |
| CYS A 345 | −13.098 | −11.530 | 0 | −11.593 | −10.171 | 0 | 0 | 0 | 0 | −6.976 | 0 | 0 |
| PRO A 346 | −13.098 | −11.530 | 0 | −11.593 | −12.171 | 0 | −13.307 | 0 | −8.472 | −6.976 | 0 | 0 |
| SER A 347 | −13.098 | −11.530 | 0 | −11.593 | −12.171 | 0 | −13.307 | 0 | −8.472 | −6.976 | 0 | 0 |
| LEU A 348 | 0 | 0 | 0 | 0 | 0 | 0 | 0 | 0 | 0 | 0 | 0 | 0 |
| ALA A 349 | −16.098 | 0 | 0 | 0 | 0 | −7.233 | 0 | −3.330 | 0 | 0 | −13.528 | −14 |
| GLY A 350 | −26.098 | −21.530 | 0 | −11.593 | −26.171 | −16.233 | −20.307 | −2.330 | −10.472 | −12.976 | −20.528 | −15 |
| LYS A 351 | −26.098 | −21.530 | 0 | −11.593 | −26.171 | 0 | −20.307 | −2.330 | −9.472 | −9.976 | −17.528 | −11 |
| PRO A 352 | 0 | 0 | 0 | 0 | 0 | 0 | 0 | 0 | 0 | 0 | 0 | −11 |
| LYS A 353 | −16.098 | 0 | 0 | 0 | 0 | −7.233 | 0 | 0 | 0 | 0 | −13.528 | −14 |
| VAL A 354 | 0 | 0 | 0 | 0 | 0 | 0 | 0 | 0 | 0 | 0 | 0 | 0 |
| PHE A 355 | 0 | 0 | 0 | 0 | 0 | 0 | 0 | 0 | 0 | 0 | 0 | 0 |
| PHE A 356 | 0 | 0 | 0 | 0 | 0 | 0 | 0 | 0 | 0 | 0 | 0 | 0 |
| ILE A 357 | 0 | 0 | 0 | 0 | 0 | 0 | 0 | 0 | 0 | 0 | 0 | 0 |
| GLN A 358 | −30.098 | 0 | −8.808 | −22.593 | −28.171 | −18.233 | −32.307 | 0 | 0 | −16.976 | −30.528 | 0 |
| ALA A 359 | −30.098 | −25.530 | −8.808 | −7.593 | −28.171 | −18.233 | −25.307 | 0 | 0 | −16.976 | −22.528 | 0 |
| CYS A 360 | −30.098 | −25.530 | −8.808 | −22.593 | −28.171 | −18.233 | −32.307 | −3.330 | 0 | −16.976 | −31.528 | 0 |
| GLN A 361 | 0 | 0 | 0 | 0 | 0 | 0 | 0 | 0 | 0 | 0 | 0 | 0 |
| GLY A 362 | 0 | 0 | −3.808 | 0 | 0 | 0 | −21.307 | 0 | 0 | −6.976 | 0 | 0 |
| ASP A 363 | −23.098 | −15.530 | −3.808 | −8.593 | −18.171 | −9.233 | −26.307 | −3.330 | −8.472 | −7.976 | −24.528 | 0 |
| ASN A 364 | −13.098 | −8.530 | −4.808 | 0 | −11.171 | −7.233 | −21.307 | 0 | −8.472 | −9.976 | −11.528 | 0 |
| TYR A 365 | −13.098 | 0 | −3.808 | 0 | 0 | −7.233 | −14.307 | 0 | −7.472 | −6.976 | −11.528 | 0 |
| GLN A 366 | −13.098 | 0 | 0 | 0 | 0 | −7.233 | −15.307 | −3.330 | −10.472 | −6.976 | −11.528 | 0 |
| LYS A 367 | −13.098 | −8.530 | −4.808 | 0 | −10.171 | −7.233 | −15.307 | −2.330 | −10.472 | −6.976 | −11.528 | 0 |
| GLY A 368 | 0 | 0 | 0 | 0 | 0 | 0 | 0 | −3.330 | 0 | 0 | 0 | 0 |
| ILE A 369 | 0 | 0 | −4.808 | 0 | 0 | 0 | 0 | −3.330 | 0 | −6.976 | 0 | 0 |
| PRO A 370 | 0 | 0 | 0 | 0 | 0 | 0 | 0 | 0 | 0 | 0 | 0 | 0 |
| VAL A 371 | −13.098 | −10.530 | 0 | 0 | 0 | 0 | 0 | −2.330 | 0 | 0 | −11.528 | 0 |
| GLU A 372 | −13.098 | 0 | 0 | 0 | 0 | 0 | 0 | 0 | 0 | 0 | −11.528 | 0 |
| THR A 373 | −13.098 | 0 | 0 | 0 | 0 | 0 | 0 | 0 | 0 | 0 | 0 | 0 |
| ASP A 374 | −13.098 | 0 | 0 | 0 | 0 | 0 | 0 | 0 | 0 | 0 | −11.528 | 0 |
| NME A 999 | 0 | 0 | 0 | 0 | 0 | 0 | 0 | 0 | 0 | 0 | 0 | 0 |
| ACE B 0 | 0 | 0 | 0 | 0 | −10.171 | 0 | 0 | 0 | 0 | 0 | 0 | 0 |
| THR B 390 | 0 | 0 | 0 | 0 | 0 | 0 | 0 | 0 | 0 | 0 | 0 | 0 |
| ARG B 391 | 0 | 0 | 0 | 0 | −11.171 | 0 | 0 | 0 | 0 | −6.976 | 0 | 0 |
| TYR B 392 | 0 | 0 | 0 | 0 | 0 | 0 | 0 | −2.330 | 0 | 0 | 0 | 0 |
| ILE B 393 | −16.098 | 0 | 0 | 0 | −23.171 | −7.233 | 0 | −3.330 | 0 | −9.976 | −13.528 | 0 |
| PRO B 394 | −16.098 | 0 | 0 | 0 | 0 | −7.233 | 0 | 0 | 0 | 0 | −13.528 | 0 |
| ASP B 395 | −16.098 | 0 | 0 | 0 | 0 | −8.233 | 0 | −2.330 | 0 | 0 | −13.528 | 0 |
| GLU B 396 | 0 | 0 | 0 | 0 | 0 | 0 | 0 | 0 | 0 | 0 | 0 | 0 |
| ALA B 397 | −16.098 | 0 | 0 | 0 | 0 | −7.233 | 0 | 0 | 0 | 0 | −13.528 | −14 |
| ASP B 398 | −16.098 | 0 | 0 | 0 | 0 | −7.233 | 0 | 0 | 0 | 0 | −13.528 | −14 |
| PHE B 399 | 0 | 0 | 0 | 0 | 0 | 0 | 0 | −4.330 | 0 | 0 | 0 | 0 |
| LEU B 400 | 0 | 0 | 0 | 0 | 0 | 0 | 0 | 0 | 0 | 0 | 0 | 0 |
| LEU B 401 | 0 | 0 | −3.808 | 0 | 0 | 0 | 0 | −3.330 | 0 | 0 | 0 | 0 |
| GLY B 402 | 0 | 0 | 0 | 0 | 0 | 0 | 0 | 0 | 0 | 0 | 0 | 0 |
| MET B 403 | 0 | 0 | 0 | 0 | 0 | 0 | 0 | 0 | 0 | 0 | 0 | 0 |
| ALA B 404 | 0 | 0 | 0 | 0 | 0 | 0 | 0 | 0 | 0 | 0 | 0 | 0 |
| THR B 405 | 0 | 0 | 0 | 0 | 0 | 0 | 0 | 0 | 0 | 0 | 0 | 0 |
| VAL B 406 | 0 | 0 | 0 | 0 | 0 | 0 | 0 | 0 | 0 | 0 | 0 | 0 |
| ASN B 407 | 0 | 0 | 0 | 0 | 0 | 0 | 0 | 0 | 0 | 0 | 0 | 0 |
| ASN B 408 | 0 | 0 | 0 | 0 | 0 | 0 | −21.307 | 0 | 0 | 0 | 0 | 0 |
| CYS B 409 | −13.098 | 0 | 0 | 0 | 0 | 0 | 0 | 0 | 0 | 0 | −11.528 | 0 |
| VAL B 410 | 0 | 0 | 0 | 0 | 0 | 0 | 0 | −2.330 | 0 | 0 | 0 | 0 |
| SER B 411 | −30.098 | −25.530 | −8.808 | −22.593 | −28.171 | −18.233 | −32.307 | 0 | 0 | −16.976 | −31.528 | 0 |
| TYR B 412 | −30.098 | 0 | −8.808 | 0 | 0 | 0 | 0 | −3.330 | 0 | −7.976 | 0 | 0 |
| ARG B 413 | −30.098 | −25.530 | −8.808 | −22.593 | −28.171 | −18.233 | −32.307 | −3.330 | −11.472 | −16.976 | −31.528 | 0 |
| ASN B 414 | 0 | −9.530 | 0 | 0 | −10.171 | 0 | 0 | −3.330 | 0 | 0 | −13.528 | 0 |

TABLE 2-continued

Fragment Binding Affinity for Caspase-8

| | acet-amide | acetone | benzene | carboxy-lic acid | dimethyl sulfoxide | ethanol | imidazole | iso-butane | pyrimi-dine | tetra-hydro-furan | urea | $H_2O$ |
|---|---|---|---|---|---|---|---|---|---|---|---|---|
| PRO B 415 | −14.098 | 0 | −8.808 | 0 | 0 | −9.233 | −15.307 | 0 | 0 | 0 | −12.528 | 0 |
| ALA B 416 | 0 | 0 | 0 | 0 | 0 | 0 | 0 | 0 | 0 | 0 | 0 | 0 |
| GLU B 417 | 0 | −9.530 | 0 | 0 | −15.171 | 0 | 0 | 0 | −15.472 | −8.976 | −13.528 | 0 |
| GLY B 418 | 0 | 0 | 0 | 0 | 0 | 0 | 0 | 0 | 0 | 0 | −13.528 | 0 |
| THR B 419 | 0 | 0 | −8.808 | 0 | −10.171 | 0 | 0 | 0 | 0 | 0 | 0 | 0 |
| TRP B 420 | 0 | −9.530 | −3.808 | 0 | −10.171 | 0 | 0 | −3.330 | −15.472 | −8.976 | −13.528 | 0 |
| TYR B 421 | 0 | 0 | 0 | 0 | 0 | 0 | 0 | 0 | 0 | 0 | 0 | 0 |
| ILE B 422 | 0 | 0 | 0 | 0 | 0 | 0 | 0 | 0 | 0 | 0 | 0 | 0 |
| GLN B 423 | −20.098 | −14.530 | −4.808 | 0 | −18.171 | 0 | −22.307 | −3.330 | −15.472 | −9.976 | −13.528 | 0 |
| SER B 424 | −21.098 | −19.530 | 0 | 0 | −18.171 | 0 | −22.307 | 0 | 0 | 0 | −20.528 | 0 |
| LEU B 425 | 0 | 0 | 0 | 0 | 0 | 0 | 0 | 0 | 0 | 0 | 0 | 0 |
| CYS B 426 | 0 | 0 | 0 | 0 | 0 | 0 | 0 | 0 | 0 | 0 | 0 | 0 |
| GLN B 427 | −21.098 | −19.530 | −3.808 | −9.593 | −18.171 | −12.233 | −22.307 | −2.330 | −12.472 | −8.976 | −22.528 | 0 |
| SER B 428 | 0 | 0 | 0 | 0 | 0 | 0 | 0 | 0 | 0 | 0 | 0 | 0 |
| LEU B 429 | 0 | 0 | 0 | 0 | 0 | 0 | 0 | 0 | 0 | 0 | 0 | 0 |
| ARG B 430 | 0 | 0 | 0 | 0 | 0 | 0 | 0 | −2.330 | 0 | 0 | 0 | 0 |
| GLU B 431 | −19.098 | −14.530 | 0 | 0 | −21.171 | −7.233 | −22.307 | 0 | −10.472 | −10.976 | −17.528 | −11 |
| ARG B 432 | 0 | 0 | 0 | 0 | −18.171 | −7.233 | 0 | 0 | 0 | 0 | −17.528 | −11 |
| CYS B 433 | 0 | 0 | 0 | 0 | 0 | 0 | 0 | 0 | 0 | 0 | 0 | 0 |
| PRO B 434 | 0 | 0 | 0 | 0 | 0 | 0 | 0 | 0 | 0 | 0 | 0 | 0 |
| ARG B 435 | −19.098 | −14.530 | 0 | 0 | −21.171 | 0 | −22.307 | 0 | −10.472 | −10.976 | −17.528 | 0 |
| GLY B 436 | 0 | 0 | 0 | 0 | −12.171 | 0 | 0 | 0 | 0 | 0 | 0 | 0 |
| ASP B 437 | −19.098 | −11.530 | 0 | −20.593 | −13.171 | 0 | 0 | 0 | −12.472 | −6.976 | −14.528 | 0 |
| ASP B 438 | −19.098 | −11.530 | 0 | −20.593 | −13.171 | −14.233 | −14.307 | 0 | −12.472 | −6.976 | −14.528 | −15 |
| ILE B 439 | 0 | 0 | 0 | 0 | 0 | 0 | 0 | 0 | 0 | 0 | 0 | 0 |
| LEU B 440 | 0 | 0 | 0 | 0 | 0 | 0 | 0 | 0 | 0 | 0 | 0 | 0 |
| THR B 441 | 0 | 0 | 0 | 0 | −13.171 | 0 | 0 | 0 | 0 | 0 | 0 | 0 |
| ILE B 442 | 0 | 0 | 0 | 0 | 0 | 0 | 0 | 0 | 0 | 0 | 0 | 0 |
| LEU B 443 | 0 | 0 | 0 | 0 | 0 | 0 | 0 | 0 | 0 | 0 | 0 | 0 |
| THR B 444 | 0 | 0 | 0 | 0 | 0 | 0 | 0 | 0 | 0 | 0 | 0 | 0 |
| GLU B 445 | 0 | 0 | 0 | 0 | 0 | −7.233 | 0 | 0 | 0 | 0 | −17.528 | −11 |
| VAL B 446 | 0 | 0 | 0 | 0 | 0 | 0 | 0 | 0 | 0 | 0 | 0 | 0 |
| ASN B 447 | 0 | 0 | 0 | 0 | 0 | 0 | 0 | 0 | 0 | 0 | 0 | 0 |
| TYR B 448 | −13.098 | 0 | 0 | 0 | 0 | −7.233 | 0 | −2.330 | 0 | 0 | −11.528 | 0 |
| GLU B 449 | −24.098 | −19.530 | 0 | −14.593 | −18.171 | −17.233 | −26.307 | 0 | −12.472 | −7.976 | −27.528 | −17 |
| VAL B 450 | 0 | 0 | 0 | 0 | 0 | 0 | 0 | 0 | 0 | 0 | 0 | 0 |
| SER B 451 | −13.098 | 0 | 0 | 0 | −10.171 | 0 | −13.307 | −3.330 | −10.472 | −6.976 | −11.528 | 0 |
| ASN B 452 | −24.098 | −10.530 | −4.808 | −11.593 | −10.171 | −9.233 | 0 | −2.330 | −10.472 | −7.976 | −27.528 | 0 |
| LYS B 453 | −24.098 | −19.530 | −5.808 | −14.593 | −18.171 | −17.233 | −26.307 | −3.330 | −15.472 | −11.976 | −27.528 | −17 |
| ASP B 454 | −16.098 | 0 | −4.808 | −12.593 | 0 | −7.233 | 0 | −2.330 | 0 | 0 | 0 | 0 |
| ASP B 455 | 0 | 0 | 0 | −7.593 | 0 | 0 | 0 | 0 | 0 | 0 | 0 | 0 |
| LYS B 456 | −16.098 | −9.530 | 0 | −12.593 | −11.171 | −7.233 | 0 | 0 | 0 | −6.976 | 0 | 0 |
| LYS B 457 | 0 | 0 | 0 | −7.593 | −11.171 | −7.233 | 0 | 0 | 0 | 0 | 0 | 0 |
| ASN B 458 | 0 | 0 | 0 | 0 | 0 | 0 | 0 | 0 | 0 | 0 | 0 | 0 |
| MET B 459 | 0 | 0 | 0 | 0 | 0 | 0 | 0 | 0 | 0 | 0 | 0 | 0 |
| GLY B 460 | 0 | 0 | 0 | 0 | 0 | 0 | 0 | 0 | 0 | 0 | 0 | 0 |
| LYS B 461 | −13.098 | −10.530 | −4.808 | −10.593 | −10.171 | −7.233 | −13.307 | −4.330 | −10.472 | −6.976 | −11.528 | 0 |
| GLN B 462 | 0 | 0 | 0 | 0 | 0 | 0 | 0 | 0 | 0 | 0 | 0 | 0 |
| MET B 463 | 0 | 0 | 0 | 0 | 0 | 0 | −13.307 | −3.330 | −10.472 | 0 | 0 | 0 |
| PRO B 464 | 0 | 0 | 0 | 0 | 0 | 0 | 0 | 0 | 0 | 0 | 0 | 0 |
| GLN B 465 | 0 | 0 | 0 | 0 | 0 | 0 | 0 | 0 | 0 | 0 | 0 | 0 |
| PRO B 466 | 0 | 0 | 0 | 0 | 0 | 0 | 0 | 0 | 0 | 0 | 0 | 0 |
| THR B 467 | 0 | 0 | 0 | 0 | 0 | 0 | 0 | 0 | 0 | 0 | 0 | 0 |
| PHE B 468 | 0 | 0 | 0 | 0 | 0 | 0 | 0 | −2.330 | 0 | 0 | 0 | 0 |
| THR B 469 | 0 | 0 | 0 | 0 | 0 | 0 | 0 | −3.330 | 0 | 0 | 0 | 0 |
| LEU B 470 | 0 | 0 | 0 | 0 | 0 | 0 | 0 | 0 | 0 | 0 | 0 | 0 |
| ARG B 471 | −20.098 | −14.530 | −3.808 | −8.593 | −23.171 | −7.233 | −23.307 | −2.330 | −11.472 | −12.976 | −16.528 | 0 |
| LYS B 472 | −26.098 | −21.530 | −4.808 | −11.593 | −26.171 | −16.233 | −21.307 | −3.330 | −14.472 | −13.976 | −20.528 | −15 |
| LYS B 473 | −21.098 | −13.530 | −3.808 | −20.593 | −13.171 | −14.233 | −14.307 | −2.330 | −12.472 | −8.976 | −14.528 | −15 |
| LEU B 474 | 0 | 0 | 0 | 0 | 0 | 0 | 0 | 0 | 0 | 0 | 0 | 0 |
| VAL B 475 | 0 | 0 | 0 | −10.593 | 0 | 0 | 0 | 0 | 0 | 0 | −19.528 | 0 |
| PHE B 476 | 0 | 0 | 0 | 0 | 0 | 0 | 0 | 0 | 0 | 0 | 0 | 0 |
| PRO B 477 | −22.098 | −12.530 | 0 | −10.593 | −16.171 | −7.233 | −22.307 | −2.330 | −9.472 | 0 | −30.528 | 0 |
| SER B 478 | 0 | 0 | 0 | 0 | 0 | 0 | 0 | 0 | 0 | 0 | 0 | 0 |
| ASP C B 479 | −22.098 | −10.530 | 0 | −13.593 | −15.171 | −15.233 | −25.307 | 0 | −9.472 | 0 | −30.528 | −14 |

While various embodiments of the present invention have been described above, it should be understood that they have been presented by way of example, and not limitation. It will be apparent to persons skilled in the relevant art that various changes in detail can be made therein without departing from the spirit and scope of the invention. Thus the present invention should not be limited by any of the above-described exemplary embodiments.

All references and publications referred to herein are hereby incorporated by reference in their entirety.

What is claimed is:

1. A method for assigning a binding affinity between polypeptide amino acid residues and one or more molecular fragments, comprising:
   (a) conducting multiple computer simulations of (i) a polypeptide comprised of amino acid residues, and (ii) at least one molecular fragment, wherein a sampling from a thermodynamically relevant ensemble of states between the polypeptide and each molecular fragment is collected, wherein multiple simulations are performed at multiple values of B and binding affinity values between fragments and residues are obtained by observing the chemical potential value at which each fragment leaves the ensemble by changing the chemical potential at constant temperature, and estimating the affinity estimated by B-critical, wherein B-critical is defined as the minimum B value for which a particular fragment is persistently observed in the vicinity of a residue, wherein B is related to the excess chemical potential of the system according to the relation $B=\mu'/kT+\ln<N>$, where $\mu'$ is the excess chemical potential, k is the Boltzmann's constant, T is the absolute temperature, and $<N>$ is the average number of molecular fragments in the simulation;
   (b) assigning a binding affinity value calculated in step (a) to at least one fragment-residue pair when said fragment of said fragment-residue pair has a finite probability to be in the vicinity of the residue of said fragment-residue pair, wherein said affinity value is an estimate of the free energy of binding between the polypeptide amino acid residue and the fragment; and
   (c) outputting a matrix of binding affinity values assigned in step (b); wherein (a) and (b) are conducted for each molecular fragment considered in the computer simulation;
   (d) repeating (a), (b) and (c) for a plurality of fragment types, wherein each fragment type belongs to at least one fragment family;
   (e) averaging the binding affinity values over a plurality of fragment families to yield a matrix of average binding affinity values, wherein the fragment family is selected from the group consisting of polar, aliphatic and heterocyclic, and
   (f) coding the three dimensional rendering of the polypeptide surface according to the matrix of average binding affinity values.

2. The method of claim 1, wherein said at least one fragment is defined as having a finite probability to be in the vicinity of a residue when at least one pair of fragment-residue atoms is within a predetermined threshold distance, wherein said threshold distance is based on the sum of the Van der Waals radii of said fragment-residue atoms.

3. The method of claim 2, wherein said predetermined threshold distance is defined as:

$$r_{ab} < \alpha(R_{VdW,a} + R_{VdW,b}),$$

wherein $r_{ab}$ is the distance between the two atoms, $R_{VdW}$ is the Van der Waals radius and $\alpha$ is a numerical parameter.

4. The method of claim 3, wherein said $\alpha$ is between about 0.5 and about 2.0.

5. The method of claim 4, wherein said $\alpha$ is about 1.2.

6. The method of claim 3, wherein said Van der Waals radius is about half the Lennard-Jones parameter $\sigma$ from the molecular-mechanics force-field considered for modeling the interaction between the polypeptide and the fragment.

7. The method of claim 6, wherein said molecular mechanics force field is selected from the group consisting of MM2, MM3, MM4, AMBER, OPLS, OPLS-AA, GROMOS, CHARMM, Xplor, Discover, MMFF and Tripos.

8. The method of claim 7, wherein said molecular mechanics force field is the AMBER force field.

9. The method of claim 1, wherein a fragment is persistently observed in the vicinity of a residue when the average number of fragments in the vicinity of the residue is greater than or equal to a fixed value between 0.8 and 1.0.

10. The method of claim 9, wherein a particular fragment is persistently observed in the vicinity of a residue when the average number of fragments in the vicinity is greater than or equal to 0.9.

11. The method of claim 1, further comprising outputting a binding analysis profile, wherein said binding analysis profile comprises a matrix of affinity values for each fragment-residue pair.

12. The method of claim 1, wherein residues with highest fragment binding affinity values are displayed with a different color from the residues with the lowest affinity value.

13. The method of claim 12, wherein sets of neighboring residues displaying high fragment binding affinities are identified as potential binding sites of the protein.

* * * * *